United States Patent
Fan et al.

(10) Patent No.: US 11,807,609 B2
(45) Date of Patent: Nov. 7, 2023

(54) DEUTERATED COMPOUNDS AS IMMUNOMODULATORS

(71) Applicant: CHEMOCENTRYX, INC., Mountain View, CA (US)

(72) Inventors: Pingchen Fan, Fremont, CA (US); Rebecca M. Lui, Mountain View, CA (US); Venkat Reddy Mali, Cupertino, CA (US); Rajinder Singh, Belmont, CA (US); Yibin Zeng, Foster City, CA (US); Penglie Zhang, Foster City, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

(21) Appl. No.: 17/066,986

(22) Filed: Oct. 9, 2020

(65) Prior Publication Data
US 2021/0276955 A1    Sep. 9, 2021

Related U.S. Application Data

(63) Continuation of application No. 16/173,914, filed on Oct. 29, 2018, now abandoned.

(60) Provisional application No. 62/578,586, filed on Oct. 30, 2017.

(51) Int. Cl.
  *C07D 211/60*  (2006.01)
  *A61K 45/06*  (2006.01)
  *A61K 31/451*  (2006.01)

(52) U.S. Cl.
  CPC .......... *C07D 211/60* (2013.01); *A61K 31/451* (2013.01); *A61K 45/06* (2013.01); *C07B 2200/05* (2013.01)

(58) Field of Classification Search
  CPC .... C07D 211/60; A61K 31/451; A61K 45/06; C07B 2200/05
  See application file for complete search history.

(56) References Cited

U.S. PATENT DOCUMENTS

| | | |
|---|---|---|
| 8,445,515 B2 | 5/2013 | Fan et al. |
| 8,906,938 B2 | 12/2014 | Fan et al. |
| 9,126,939 B2 | 9/2015 | Fan et al. |
| 9,573,897 B2 | 2/2017 | Fan et al. |
| 10,035,768 B2 | 7/2018 | Fan et al. |
| 2010/0311753 A1 | 12/2010 | Fan et al. |
| 2011/0275639 A1* | 11/2011 | Fan ............... C07D 401/06 514/330 |
| 2013/0028870 A1 | 1/2013 | Royal et al. |
| 2015/0141425 A1 | 5/2015 | Fan et al. |
| 2016/0090357 A1 | 3/2016 | Fan et al. |
| 2017/0065604 A1 | 3/2017 | Fan et al. |
| 2017/0114017 A1 | 4/2017 | Fan et al. |
| 2017/0283446 A1 | 10/2017 | Fan et al. |
| 2019/0144389 A1 | 5/2019 | Fan et al. |

FOREIGN PATENT DOCUMENTS

| | | |
|---|---|---|
| WO | 02/049993 A2 | 6/2002 |
| WO | 02/049993 A3 | 6/2002 |
| WO | 03/029187 A1 | 4/2003 |
| WO | 03/082826 A1 | 10/2003 |
| WO | 03/082828 A1 | 10/2003 |
| WO | 03/084524 A1 | 10/2003 |
| WO | 2004/018460 A1 | 3/2004 |
| WO | 2004/043925 A2 | 5/2004 |
| WO | 2004/043925 A3 | 5/2004 |
| WO | 2004/100975 A1 | 11/2004 |
| WO | 2005/007087 A2 | 1/2005 |
| WO | 2005/007087 A3 | 1/2005 |
| WO | 2010/075257 A1 | 7/2010 |
| WO | 2011/163640 A2 | 12/2011 |

OTHER PUBLICATIONS

Bekker et al. (PLOS ONE (Oct. 21, 2016) pp. 1-19). (Year: 2016).*
Tung (Concert Pharmaceuticals (2010) pp. 1-4). (Year: 2010).*
International Search Report and Written Opinion dated Jan. 15, 2019 corresponding to PCT/US2018/058027 filed Oct. 29, 2018 (15 pages).
Extended European Search Report dated Mar. 9, 2021 corresponding to EP18874874.3 filed Oct. 29, 2018; 6 pages.
Pubchem CID: 3401926 create date Aug. 9, 2005; 13 pages.
Strachan A.J. et al., "A New Small Molecule C5a Receptor Antagonist Inhibits the Reverse-Passive Arthus Reaction and Endotoxic Shock in Rats," The Journal of Immunology, (Apr. 6, 2000); 164:6560-6565.

(Continued)

*Primary Examiner* — Marcos L Sznaidman
(74) *Attorney, Agent, or Firm* — Mintz Levin Cohn Ferris Glovsky and Popeo PC

(57) ABSTRACT

Compounds are provided to modulate the C5a receptor. The compounds have the following Formula (I):

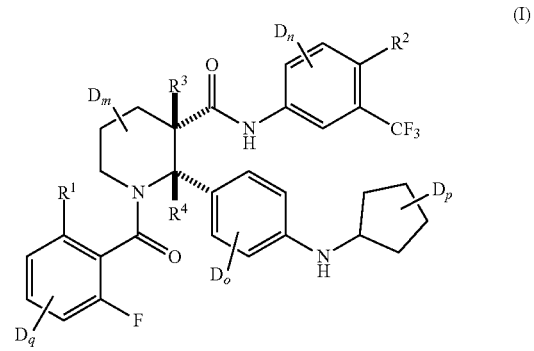

including stereoisomers and pharmaceutically acceptable salts thereof, wherein $R^1$, $R^2$ and $R^3$ are as defined herein. Methods associated with preparation and use of such compounds, as well as pharmaceutical compositions comprising such compounds, are also disclosed.

2 Claims, No Drawings

(56) References Cited

OTHER PUBLICATIONS

Woodruff T.M. et al., "A Potent Human C5a Receptor Antagonist Protects against Disease Pathology in a Rat Model of Inflammatory Bowel Disease," *The Journal of Immunology* (Nov. 15, 2003); 171:5514-5520.

* cited by examiner

DEUTERATED COMPOUNDS AS IMMUNOMODULATORS

CROSS-REFERENCES TO RELATED APPLICATIONS

This application is a continuation of U.S. patent application Ser. No. 16/173,914 filed Oct. 29, 2018, which is an application claiming priority benefit under 35 U.S.C. § 119(e) of U.S. Provisional Application No. 62/578,586 filed Oct. 30, 2017, each of which is herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The complement system plays a central role in the clearance of immune complexes and in immune responses to infectious agents, foreign antigens, virus infected cells and tumor cells. Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers, In Clinical Immunology: Principles and Practice, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., J. Exp. Med. 176: 1497-1502 (1992); Suankratay, C. et al., J. Immunol. 160: 3006-3013 (1998)).

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., J. Immunol. 99: 1211-1216 (1967)). It is composed of two polypeptide chains, α and β, with approximate molecular weights of 115 kD and 75 kD, respectively (Tack, B. F. et al., Biochemistry 18: 1490-1497 (1979)). Biosynthesized as a single-chain promolecule, C5 is enzymatically cleaved into a two-chain structure during processing and secretion. After cleavage, the two chains are held together by at least one disulphide bond as well as noncovalent interactions (Ooi, Y. M. et al., J. Immunol. 124: 2494-2498 (1980)).

C5 is cleaved into the C5a and C5b fragments during activation of the complement pathways. The convertase enzymes responsible for C5 activation are multi-subunit complexes of C4b, C2a, and C3b for the classical pathway and of (C3b)2, Bb, and P for the alternative pathway (Goldlust, M. B. et al., J. Immunol. 113: 998-1007 (1974); Schreiber, R. D. et al, Proc. Natl. Acad. Sci. 75: 3948-3952 (1978)). C5 is activated by cleavage at position 74-75 (Arg-Leu) in the α-chain. After activation, the 11.2 kD, 74 amino acid peptide C5a from the amino-terminus portion of the α-chain is released. Both C5a and C3a are potent stimulators of neutrophils and monocytes (Schindler, R. et al., Blood 76: 1631-1638 (1990); Haeffner-Cavaillon, N. et al., J. Immunol. 138: 794-700 (1987); Cavaillon, J. M. et al., Eur. J. Immunol. 20: 253-257 (1990)).

In addition to its anaphylatoxic properties, C5a induces chemotactic migration of neutrophils (Ward, P. A. et al., J. Immunol. 102: 93-99 (1969)), eosinophils (Kay, A. B. et al., Immunol. 24: 969-976 (1973)), basophils (Lett-Brown, M. A. et al., J. Immunol. 117: 246-252 1976)), and monocytes (Snyderman, R. et al., Proc. Soc. Exp. Biol. Med. 138: 387-390 1971)). Both C5a and C5b-9 activate endothelial cells to express adhesion molecules essential for sequestration of activated leukocytes, which mediate tissue inflammation and injury (Foreman, K. E. et al., J. Clin. Invest. 94: 1147-1155 (1994); Foreman, K. E. et al., Inflammation 20: 1-9 (1996); Rollins, S. A. et al., Transplantation 69: 1959-1967 (2000)). C5a also mediates inflammatory reactions by causing smooth muscle contraction, increasing vascular permeability, inducing basophil and mast cell degranulation and inducing release of lysosomal proteases and oxidative free radicals (Gerard, C. et al., Ann. Rev. Immunol. 12: 775-808 (1994)). Furthermore, C5a modulates the hepatic acute-phase gene expression and augments the overall immune response by increasing the production of TNF-α, IL-1-β, IL-6, IL-8, prostaglandins and leukotrienes (Lambris, J. D. et al., In: The Human Complement System in Health and Disease, Volanakis, J. E. ed., Marcel Dekker, New York, pp. 83-118).

The anaphylactic and chemotactic effects of C5a are believed to be mediated through its interaction with the C5a receptor. The human C5a receptor (C5aR) is a 52 kD membrane bound G protein-coupled receptor, and is expressed on neutrophils, monocytes, basophils, eosinophils, hepatocytes, lung smooth muscle and endothelial cells, and renal glomerular tissues (Van-Epps, D. E. et al., J. Immunol. 132: 2862-2867 (1984); Haviland, D. L. et al., J. Immunol. 154:1861-1869 (1995); Wetsel, R. A., Immunol.

Leff. 44: 183-187 (1995); Buchner, R. R. et al., *J. Immunol.* 155: 308-315 (1995); Chenoweth, D. E. et al., *Proc. Natl. Acad. Sci.* 75: 3943-3947 (1978); Zwirner, J. et al., *Mol. Immunol.* 36:877-884 (1999)). The ligand-binding site of C5aR is complex and consists of at least two physically separable binding domains. One binds the C5a amino terminus (amino acids 1-20) and disulfide-linked core (amino acids 21-61), while the second binds the C5a carboxyterminal end (amino acids 62-74) (Wetsel, R. A., *Curr. Opin. Immunol.* 7: 48-53 (1995)).

C5a plays important roles in inflammation and tissue injury. In cardiopulmonary bypass and hemodialysis, C5a is formed as a result of activation of the alternative complement pathway when human blood makes contact with the artificial surface of the heart-lung machine or kidney dialysis machine (Howard, R. J. et al., *Arch. Surg.* 123: 1496-1501 (1988); Kirklin, J. K. et al., *J. Cardiovasc. Surg.* 86: 845-857 (1983); Craddock, P. R. et al., *N. Engl. J. Med.* 296: 769-774 (1977)). C5a causes increased capillary permeability and edema, bronchoconstriction, pulmonary vasoconstriction, leukocyte and platelet activation and infiltration to tissues, in particular the lung (Czermak, B. J. et al., *J Leukoc. Biol.* 64: 40-48 (1998)). Administration of an anti-C5a monoclonal antibody was shown to reduce cardiopulmonary bypass and cardioplegia-induced coronary endothelial dysfunction (Tofukuji, M. et al., *J. Thorac. Cardiovasc. Surg.* 116: 1060-1068 (1998)).

C5a is also involved in acute respiratory distress syndrome (ARDS), Chronic Obstructive Pulmonary Disorder (COPD) and multiple organ failure (MOF) (Hack, C. E. et al., *Am. J. Med.* 1989: 86: 20-26; Hammerschmidt D E et al. *Lancet* 1980; 1: 947-949; Heideman M. et al. *J. Trauma* 1984; 4: 1038-1043; Marc, M M, et al., *Am. J. Respir. Cell and Mol. Biol.,* 2004: 31: 216-219). C5a augments monocyte production of two important pro-inflammatory cytokines, TNF-α and IL-1. C5a has also been shown to play an important role in the development of tissue injury, and particularly pulmonary injury, in animal models of septic shock (Smedegard G et al. *Am. J. Pathol.* 1989; 135: 489-497; Markus, S., et al., *FASEB Journal* (2001), 15: 568-570). In sepsis models using rats, pigs and non-human primates, anti-C5a antibodies administered to the animals before treatment with endotoxin or *E. coli* resulted in decreased tissue injury, as well as decreased production of IL-6 (Smedegard, G. et al., *Am. J. Pathol.* 135: 489-497 (1989); Hopken, U. et al., *Eur. J. Immunol.* 26: 1103-1109 (1996); Stevens, J. H. et al., *J. Clin. Invest.* 77: 1812-1816 (1986)). More importantly, blockade or C5a with anti-C5a polyclonal antibodies has been shown to significantly improve survival rates in a caecal ligation/puncture model of sepsis in rats (Czermak, B. J. et al., Nat. Med. 5: 788-792 (1999)). This model share many aspects of the clinical manifestation of sepsis in humans. (Parker, S. J. et al., *Br. J. Surg.* 88: 22-30 (2001)). In the same sepsis model, anti-C5a antibodies were shown to inhibit apoptosis of thymocytes (Guo, R. F. et al., *J. Clin. Invest.* 106: 1271-1280 (2000)) and prevent MOF (Huber-Lang, M. et al., *J. Immunol.* 166: 1193-1199 (2001)). Anti-C5a antibodies were also protective in a cobra venom factor model of lung injury in rats, and in immune complex-induced lung injury (Mulligan, M. S. et al. *J. Clin. Invest.* 98: 503-512 (1996)). The importance of C5a in immune complex-mediated lung injury was later confirmed in mice (Bozic, C. R. et al., *Science* 26: 1103-1109 (1996).

C5a is found to be a major mediator in myocardial ischemia-reperfusion injury. Complement depletion reduced myocardial infarct size in mice (Weisman, H. F. et al., *Science* 249: 146-151 (1990)), and treatment with anti-C5a antibodies reduced injury in a rat model of hindlimb ischemia-reperfusion (Bless, N. M. et al., *Am. J. Physiol.* 276: L57-L63 (1999)). Reperfusion injury during myocardial infarction was also markedly reduced in pigs that were retreated with a monoclonal anti-C5a IgG (Amsterdam, E. A. et al., *Am. J. Physiol.* 268:H448-H457 (1995)). A recombinant human C5aR antagonist reduces infarct size in a porcine model of surgical revascularization (Riley, R. D. et al., *J. Thorac. Cardiovasc. Surg.* 120: 350-358 (2000)).

C5a driven neutrophils also contribute to many bullous diseases (e.g., bullous pemphigoid, pemphigus vulgaris and pemphigus foliaceus). These are chronic and recurring inflammatory disorders clinically characterized by sterile blisters that appear in the sub-epidermal space of the skin and mucosa. While autoantibodies to keratinocytes located at the cutaneous basement membranes are believed to underlie the detachment of epidermal basal keratinocytes from the underlying basement membrane, blisters are also characterized by accumulation of neutrophils in both the upper dermal layers and within the blister cavities. In experimental models a reduction of neutrophils or absence of complement (total or C5-selective) can inhibit formation of sub-epidermal blisters, even in the presence of high auto-antibody titers.

Complement levels are elevated in patients with rheumatoid arthritis (Jose, P. J. et al., *Ann. Rheum. Dis.* 49: 747-752 (1990); Grant, E. P., et al., *J. of Exp. Med.,* 196(11): 1461-1471, (2002)), lupus nephritis (Bao, L., et al., *Eur. J. of Immunol.,* 35(8), 2496-2506, (2005)) and systemic lupus erythematosus (SLE) (Porcel, J. M. et al., *Clin. Immunol. Immunopathol.* 74: 283-288 (1995)). C5a levels correlate with the severity of the disease state. Collagen-induced arthritis in mice and rats resembles the rheumatoid arthritic disease in human. Mice deficient in the C5a receptor demonstrated a complete protection from arthritis induced by injection of monoclonal anti-collagen Abs (Banda, N. K., et al., J. of Immunol., 2003, 171: 2109-2115). Therefore, inhibition of C5a and/or C5a receptor (C5aR) could be useful in treating these chronic diseases.

The complement system is believed to be activated in patients with inflammatory bowel disease (IBD) and is thought to play a role in the disease pathogenesis. Activated complement products were found at the luminal face of surface epithelial cells, as well as in the muscularis mucosa and submucosal blood vessels in IBD patients (Woodruff, T .M., et al., *J of Immunol.,* 2003, 171: 5514-5520).

C5aR expression is upregulated on reactive astrocytes, microglia, and endothelial cells in an inflamed human central nervous system (Gasque, P. et al., *Am. J. Pathol.* 150: 31-41 (1997)). C5a might be involved in neurodegenerative diseases, such as Alzheimer disease (Mukherjee, P. et al., *J. Neuroimmunol.* 105: 124-130 (2000); O'Barr, S. et al., *J. Neuroimmunol.* (2000) 105: 87-94; Farkas, I., et al. *J. Immunol.* (2003) 170:5764-5771), Parkinson's disease, Pick disease and transmissible spongiform encephalopathies. Activation of neuronal C5aR may induce apoptosis (Farkas I et al. *J. Physiol.* 1998; 507: 679-687). Therefore, inhibition of C5a and/or C5aR could also be useful in treating neurodegenerative diseases.

There is some evidence that C5a production worsens inflammation associated with atopic dermatitis (Neuber, K., et al., *Immunology* 73:83-87, (1991)), and chronic urticaria (Kaplan, A. P., *J. Allergy Clin. Immunol.* 114; 465-474, (2004).

Psoriasis is now known to be a T cell-mediated disease (Gottlieb, E. L. et al., *Nat. Med.* 1: 442-447 (1995)). However, neutrophils and mast cells may also be involved in the pathogenesis of the disease (Terui, T. et al., *Exp. Dermatol.* 9: 1-10; 2000); Werfel, T. et al., *Arch. Dermatol. Res.* 289: 83-86 (1997)). Neutrophil accumulation under the stratum corneum is observed in the highly inflamed areas of psoriatic plaques, and psoriatic lesion (scale) extracts contain highly elevated levels of C5a and exhibit potent chemotactic activity towards neutrophils, an effect that can be inhibited by addition of a C5a antibody. T cells and neutrophils are chemo-attracted by C5a (Nataf, S. et al., *J. Immunol.* 162: 4018-4023 (1999); Tsuji, R. F. et al., *J. Immunol.* 165: 1588-1598 (2000); Cavaillon, J. M. et al., *Eur. J. Immunol.* 20: 253-257 (1990)). Additionally expression of C5aR has been demonstrated in plasmacytoid dendritic cells (pDC) isolated from lesions of cutaneous lupus erythematous and these cells were shown to display chemotactic behavior towards C5a, suggesting that blockade of C5aR on pDC might be efficacious in reducing pDC infiltration into inflamed skin in both SLE and psoriasis. Therefore C5a could be an important therapeutic target for treatment of psoriasis.

Immunoglobulin G-containing immune complexes (IC) contribute to the pathophysiology in a number of autoimmune diseases, such as systemic lupus erthyematosus, rheumatoid arthritis, Sjogren's disease, Goodpasture's syndrome, and hypersensitivity pneumonitis (Madaio, M. P., *Semin. Nephrol.* 19: 48-56 (1999); Korganow, A. S. et al., *Immunity* 10: 451-459 (1999); Bolten, W. K., *Kidney Int.* 50: 1754-1760 (1996); Ando, M. et al., *Curr. Opin. Pulm. Med.* 3: 391-399 (1997)). These diseases are highly heterogeneous and generally affect one or more of the following organs: skin, blood vessels, joints, kidneys, heart, lungs, nervous system and liver (including cirrhosis and liver fibrosis). The classical animal model for the inflammatory response in these IC diseases is the Arthus reaction, which features the infiltration of polymorphonuclear cells, hemorrhage, and plasma exudation (Arthus, M., *C.R. Soc. Biol.* 55: 817-824 (1903)). Recent studies show that C5aR deficient mice are protected from tissue injury induced by IC (Kohl, J. et al., *Mol. Immunol.* 36: 893-903 (1999); Baumann, U. et al., *J. Immunol.* 164: 1065-1070 (2000)). The results are consistent with the observation that a small peptidic anti-C5aR antagonist inhibits the inflammatory response caused by IC deposition (Strachan, A. J. et al., *J. Immunol.* 164: 6560-6565 (2000)). Together with its receptor, C5a plays an important role in the pathogenesis of IC diseases. Inhibitors of C5a and C5aR could be useful to treat these diseases.

DESCRIPTON OF RELATED ART

Non-peptide based C5a receptor antagonist have been reported as being effective for treating endotoxic shock in rats (Stracham, A. J., et al., *J. of Immunol.* (2000), 164(12): 6560-6565); and for treating IBD in a rat model (Woodruff, T. M., et al., *J. of Immunol.*, 2003, 171: 5514-5520). Non-peptide based C5a receptor modulators also have been described in the patent literature by Neurogen Corporation, (e.g., WO2004/043925, WO2004/018460, WO2005/007087, WO03/082826, WO03/08828, WO02/49993, WO03/084524); Dompe S. P. A. (WO02/029187); The University of Queenland (WO2004/100975); and ChemoCentryx (WO2010/075257).

There is considerable experimental evidence in the literature that implicates increased levels of C5a with a number of diseases and disorders, in particular in autoimmune and inflammatory diseases and disorders. Thus, there remains a need in the art for new small organic molecule modulators, e.g., agonists, preferably antagonists, partial agonists, of the C5a receptor (C5aR) that are useful for inhibiting pathogenic events, e.g., chemotaxis, associated with increased levels anaphylatoxin activity. The present invention fulfills this and other needs.

BRIEF SUMMARY OF THE INVENTION

In one aspect, provided herein are compounds having formula (I):

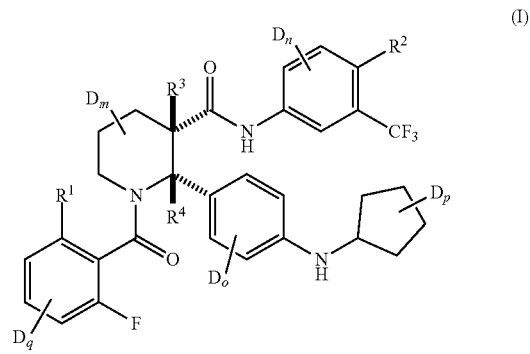

or a pharmaceutically acceptable salt thereof, wherein:
$R^1$ is selected from the group consisting of $CH_3$, $CH_2D$, $CHD_2$, and $CD_3$, and $CD_2OH$;
$R^2$ is selected from the group consisting of $CH_3$, $CH_2D$, $CHD_2$, $CD_3$, $CH_2OH$, $CDHOH$, and $CD_2OH$;
$R^3$ is H or D;
$R^4$ is H or D;
m is an integer from 0-6;
n is an integer from 0-3;
o is an integer from 0-4;
p is an integer from 0-9; and
q is an integer from 0-3;
and wherein said compound has at least one deuterium atom present in an amount of at least 80%.

In addition to the compounds provided herein, the present invention further provides pharmaceutical compositions containing one or more of these compounds, as well as methods for the use of these compounds in therapeutic methods, primarily to treat diseases associated with C5a signaling activity.

BRIEF DESCRIPTION OF THE DRAWINGS

NOT APPLICABLE

DETAILED DESCRIPTION OF THE INVENTION

I. Abbreviation and Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "pharmaceutically acceptable salt" is meant to include salts of the active compounds which are prepared with relatively nontoxic acids or bases, depending on the particular substituents found on the compounds described herein. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19).

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

As used herein, a line drawn to the interior of a ring is meant to indicate attachment at any available site on the ring.

II. COMPOUNDS

In one aspect, the present invention provides compounds having Formula (I):

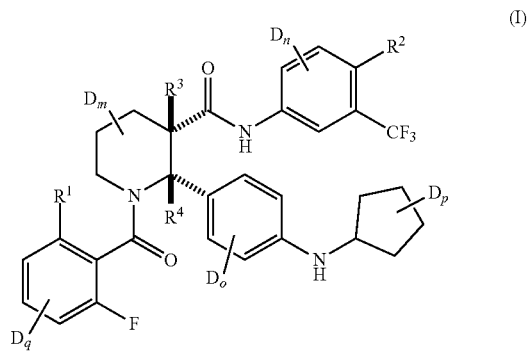

or a pharmaceutically acceptable salt thereof, wherein:
  $R^1$ is selected from the group consisting of $CH_3$, $CH_2D$, $CHD_2$, and $CD_3$, and $CD_2OH$;
  $R^2$ is selected from the group consisting of $CH_3$, $CH_2D$, $CHD_2$, $CD_3$, $CH_2OH$, $CDHOH$, and $CD_2OH$;
  $R^3$ is H or D;
  $R^4$ is H or D;
  m is an integer from 0-6;
  n is an integer from 0-3;
  o is an integer from 0-4;
  p is an integer from 0-9; and
  q is an integer from 0-3;
  and wherein said compound has at least one deuterium atom present in an amount of at least 80%.

In some embodiments, compounds of Formula (I) are provided, or a pharmaceutically acceptable salt thereof, wherein $R^1$ is selected from the group consisting of $CH_3$ and $CD_3$.

In some embodiments, compounds of Formula (I) are provided, or a pharmaceutically acceptable salt thereof, wherein $R^2$ is selected from the group consisting of $CH_3$, $CD_3$, $CH_2OH$ and $CD_2OH$.

In some embodiments, compounds of Formula (I) are provided, or a pharmaceutically acceptable salt thereof, wherein $R^3$ is D.

In some embodiments, compounds of Formula (I) are provided, or a pharmaceutically acceptable salt thereof, wherein $R^3$ and $R^4$ are each H.

In some embodiments, compounds of Formula (I) are provided, or a pharmaceutically acceptable salt thereof, wherein the subscript n is 0, 1 or 2.

In some embodiments, compounds of Formula (I) are provided, or a pharmaceutically acceptable salt thereof, wherein the subscript o is 0 or 1.

In some embodiments, compounds of Formula (I) are provided, or a pharmaceutically acceptable salt thereof, wherein the subscript q is 0 or 1.

In some embodiments, compounds of Formula (I) are provided, or a pharmaceutically acceptable salt thereof, wherein the subscript p is 0, 1, 4 or 9.

In some embodiments, compounds of Formula (I) are provided, or a pharmaceutically acceptable salt thereof, wherein the subscript m is 0.

In some embodiments, compounds of Formula (I) are provided, or a pharmaceutically acceptable salt thereof, wherein the subscript m is 0; the subscript n is 0,1 or 2; the subscript o is 0 or 1; the subscript p is 0, 1, 4 or 9; and the subscript q is 0 or 1.

In some embodiments, compound of Formula (I) are provided, or a pharmaceutically acceptable salt thereof, wherein said compound has at least two deuterium atoms present in an amount of at least 80% for each deuterated position. In some embodiments, compound of Formula (I) are provided, or a pharmaceutically acceptable salt thereof, wherein said compound has at least three deuterium atoms present in an amount of at least 80% for each deuterated position. In some embodiments, compound of Formula (I) are provided, or a pharmaceutically acceptable salt thereof, wherein said compound has at least four deuterium atoms present in an amount of at least 80% for each deuterated position. In some embodiments, compound of Formula (I) are provided, or a pharmaceutically acceptable salt thereof, wherein said compound has at least five deuterium atoms present in an amount of at least 80% for each deuterated position.

The relative amount of deuterium at each deuterated position can vary. In some embodiments, a deuterium atom is present in an amount of at least 80, 85, 90, 95, 97, or 99% for each deuterated position. In some embodiments, a deuterium atom is present in an amount of at least 85% for each deuterated position. In some embodiments, a deuterium atom is present in an amount of at least 90% for each deuterated position. In some embodiments, a deuterium atom is present in an amount of at least 95% for each deuterated position. In some embodiments, a deuterium atom is present in an amount of at least 97% for each deuterated position. In some embodiments, a deuterium atom is present in an amount of at least 99% for each deuterated position.

In addition to the compounds provided above, pharmaceutically acceptable salts of those compounds are also provided. In some embodiments, the pharmaceutically acceptable salts are selected from hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids.

III. PHARMACEUTICAL COMPOSITIONS

In addition to the compounds provided above, compositions for modulating C5a activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stent-graft device.

The pharmaceutical compositions of the present disclosure may be formulated with one or more additional therapeutic agents. The one or more additional therapeutic agents can include corticosteroids, steroids, immunosuppressants, or CD 20 inhibitors. In some embodiments, the one or more additional therapeutic agents include obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIIB-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, LT-1951, OMS721, ALN-CC5, ACH-4471, AMY-101, Acthar gel, and CD4+CD25+ regulatory T-cells, MEDI7814, P32, P59, CCX354, CCX721, CCX9588, CCX140, CCX872, CCX598, CCX6239, CCX587, CCX624, CCX282, CCX025, CCX507, CCX430, CCX765, CCX758, CCX771, CCX662, CCX650, and combinations thereof. In certain selected embodiments, the additional agent is selected from obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate. Further discussions of combination therapy are included in the "Methods of Use" section of this application. In some embodiments, the additional agents are formulated separately and/or provided in "kit" form and with the deuterated compounds provided herein.

IV. METHODS OF USE

The compounds of the invention may be used as agonists, (preferably) antagonists, partial agonists, inverse agonists, of C5a receptors in a variety of contexts, both in vitro and in vivo. In one embodiment, the compounds of the invention are C5aR antagonist that can be used to inhibit the binding of C5a receptor ligand (e.g., C5a) to C5a receptor in vitro or in vivo. In general, such methods comprise the step of contacting a C5a receptor with a sufficient amount of one or more C5a receptor modulators as provided herein, in the presence of C5a receptor ligand in aqueous solution and under conditions otherwise suitable for binding of the ligand to C5a receptor. The C5a receptor may be present in suspension (e.g., in an isolated membrane or cell preparation), in a cultured or isolated cell, or in a tissue or organ.

Preferably, the amount of C5a receptor modulator contacted with the receptor should be sufficient to inhibit C5a binding to C5a receptor in vitro as measured, for example, using a radioligand binding assay, calcium mobilization assay, or chemotaxis assay as described herein.

In one embodiment of the invention, the C5a modulators of the invention are used to modulate, preferably inhibit, the signal-transducing activity of a C5a receptor, for example, by contacting one or more compound(s) of the invention with a C5a receptor (either in vitro or in vivo) under conditions suitable for binding of the modulator(s) to the receptor. The receptor may be present in solution or suspension, in a cultured or isolated cell preparation or within a patient. Any modulation of the signal transducing activity may be assessed by detecting an effect on calcium ion calcium mobilization or by detecting an effect on C5a receptor-mediated cellular chemotaxis. In general, an effective amount of C5a modulator(s) is an amount sufficient to modulate C5a receptor signal transducing activity in vitro within a calcium mobilization assay or C5a receptor-mediated cellular chemotaxis within a migration assay.

When compounds of the invention are used to inhibit C5a receptor-mediated cellular chemotaxis, preferably leukocyte (e.g., neutrophil) chemotaxis, in an in vitro chemotaxis assay, such methods comprise contacting white blood cells (particularly primate white blood cells, especially human white blood cells) with one or more compounds of the invention. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound of the invention has been added.

In another embodiment, the compounds of the present invention further can be used for treating patients suffering from conditions that are responsive to C5a receptor modulation. As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). As used herein, a condition is considered "responsive to C5a receptor modulation" if modulation of C5a receptor activity results in the reduction of inappropriate activity of a C5a receptor. As used herein, the term "patients" include primates (especially humans), domesticated companion animals (such as dogs, cats, horses, and the like) and livestock (such as cattle, pigs, sheep, and the like), with dosages as described herein.

Conditions That can be Treated by C5a Modulation:

Autoimmune disorders—e.g., Rheumatoid arthritis, systemic lupus erythematosus, Guillain-Barre syndrome, pancreatitis, lupus nephritis, lupus glomerulonephritis, psoriasis, Crohn's disease, vasculitis, irritable bowel syndrome, dermatomyositis, multiple sclerosis, bronchial asthma, dense deposit disease, pemphigus, pemphigoid, scleroderma, myasthenia gravis, autoimmune hemolytic and thrombocytopenic states, Goodpasture's syndrome (and associated glomerulonephritis and pulmonary hemorrhage), C3-glomerulopathy, C3-glomerulonephritis, membranoproliferative glomerulonephritis, Kawasaki disease, IGs nephropathy, immunovasculitis, tissue graft rejection, graft versus host disease, hyperacute rejection of transplanted organs; and the like.

Inflammatory disorders and related conditions—e.g., Neutropenia, sepsis, septic shock, Alzheimer's disease, multiple sclerosis, neutrophilia, stroke, inflammatory bowel disease (IBD), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS), Hemolytic uremic syndrome, hidradenitis suppurativa, and atypical hemolytic uremic syndrome (aHUS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. Compounds of the instant invention may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a compound of the invention may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Oncologic Diseases or Disorders—e.g., melanoma, lung cancer, lymphoma, sarcoma, carcinoma, fibrosarcoma, liposarcoma, chondrosarcoma, osteogenic sarcoma, angiosarcoma, lymphangiosarcoma, synovioma, mesothelioma, meningioma, leukemia, lymphoma, leiomyosarcoma, rhabdomyosarcoma, squamous cell carcinoma, basal cell carcinoma, adenocarcinoma, papillary carcinoma, cystadenocarcinoma, bronchogenic carcinoma, renal cell carcinoma, hepatocellular carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

Diseases of Vasculitis—Vasculitic dseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The compounds provided in the present invention can be used to treat leukoclastic vasculitis, Anti-neutrophil cytoplasmic antibody (ANCA) associated vasculitis, immune vasculitis Wegener's granulomatosis, microscopic polyangiitis, Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS—C5a receptor modulators provided herein may be used to inhibit HIV infection, delay AIDS progression or decrease the severity of symptoms or HIV infection and AIDS.

Neurodegenerative disorders and related diseases— Within further aspects, C5a antagonists provided herein may be used to treat Alzheimer's disease, multiple sclerosis, and cognitive function decline associated with cardiopulmonary bypass surgery and related procedures.

In one embodiment of the invention, the compounds of the invention can be used for the treatment of diseases selected from the group consisting of sepsis (and associated disorders), COPD, rheumatoid arthritis, lupus nephritis and multiple sclerosis.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the invention are preferably administered to a patient (e.g., a human) orally or topically. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Combination Therapy

The presently disclosed compounds may be used in combination with one or more additional therapeutic agents that are used in the treatment, prevention, suppression or amelioration of the diseases or conditions for which compounds and compositions of the present invention are useful. Such one or more additional therapeutic agents may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention.

Examples of the one or more additional therapeutic agents that may be combined with a compound or composition of the present invention, either administered separately or in the same pharmaceutical compositions, include, but are not limited to: corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, C3aR modulators, C5aR2 modulators, T cell receptor antagonists, antagonists of the chemokine receptors, especially CXCR1, CXCR2, CXCR3, CXCR4, CXCR7, CCR1, CCR2, CCR3, CCR4, CCR5, CCR7, CCR7, CCR9, CX3CR1 and CXCR6, and combinations thereof. In some embodiments, the additional agents is selected from: (a) VLA-4 antagonists, (b) steroids and corticosteroids, such as beclomethasone, betamethasone (including betamethasone sodium phosphate, betamethasone valerate, betamethasone dipropionate) prednisone, prenisolone, methylprednisolone, mometasone, dexamethasone (including dexamethasone sodium phosphate), fluticasone, cortisone (including cortisone acetate) hydrocortisone (including hydrocortisone acetate, hydrocortisone-17-valerate, hydrocortisone-17-butyrate, hydrocortisone-17-aceponate, hydrocortisone-17-buteprate), budesonide, desonide, fluocinonide (including fluocinolone acetonide), triamcinolone (including triamcinolone acetonide and triamcinolone alcohol), tixocortol (including tixocortol pivalate) fluocortolone (including fluocortolone caproate and fluocortolone pivalate), amcinonide, halcinonide, halometasone, fluprednidene acetate, salmeterol, salmeterol, salbutamol, ciclesonide, formeterol, alclometasone (including alclometasone dipropionate), prednicarbate, clobetasone (including clobetasone-17-butrate), clobetasol (including clobetasol-17-propionate); (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and rnycophenolate, e.g., mycophenolate mofetil (CellCept8); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106, 203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, rniroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbre10), (k) cyclophosphamide, (l) antibody therapies such as orthoclone (OKT3), daclizumab (Zenapax®), basiliximab (Simulect®) and infliximab (Remicade®), (m) antibody therapies targeting CD20 such as obinutuzumab, rituximab, or ocrelizumab; (n) chemotherapeutic agents such anthracyclines (e.g., daunorubicin (daunomycin; rubidomycin), doxorubicin, epirubicin, idarubicin, and valrubicin), mitoxantrone, and pixantrone; platinum-based agents (e.g., cisplatin, carboplatin, oxaliplatin, satraplatin, picoplatin, nedaplatin, triplatin, and lipoplatin); tamoxifen and metabolites thereof such as 4-hydroxytamoxifen (afimoxifene) and N-desmethyl-4-hydroxytamoxifen (endoxifen); taxanes such as paclitaxel (taxol) and docetaxel; alkylating agents (e.g., nitrogen mustards such as mechlorethamine (HN2), cyclophosphamide, ifosfamide, melphalan (L-sarcolysin), and chlorambucil); ethylenimines and methylmelamines (e.g., hexamethylmelamine, thiotepa, alkyl sulphonates such as busulfan, nitrosoureas such as carmustine (BCNU), lomustine (CCNLJ), semustine (methyl-CCN-U), and streptozoein (streptozotocin), and triazenes such as decarbazine (DTIC; dimethyltriazenoimidazole-carboxamide)); antimetabolites (e.g., folic acid analogues such as methotrexate (amethopterin), pyrimidine analogues such as fluorouracil (5-fluorouracil; 5-FU), floxuridine (fluorodeoxyuridine; FUdR), and cytarabine (cytosine arabinoside), and purine analogues and related inhibitors such as mercaptopurine (6-mercaptopurine; 6-MP), thioguanine (6-thioguanine; 6-TG), and pentostatin (2'-deoxycofonnycin)); (o) other antagonists of the chemokine receptors, especially CXCR1, CXCR2, CXCR3, CXCR4, CXCR7, CCR1, CCR2, CCR3, CCR4, CCR5, CCR7, CCR9, CX3CR1 and CXCR6.

In some embodiments, the additional therapeutic agents is selected from CCX354, CCX721, CCX9588, CCX140, CCX872, CCX598, CCX6239, CCX587, CCX624, CCX282, CCX025, CCX507, CCX430, CCX765, CCX758, CCX771, CCX662, and CCX650, and combinations thereof.

The disease or disorder being treated will determine which additional therapeutic agent or therapeutic agents are most appropriately administered in combination with the compounds of the present invention - such determination can be made by a person of skill in the art.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Non-Pharmaceutical Applications

In another aspect of the invention, the compounds of the invention can be used in a variety of non-pharmaceutical in vitro and in vivo application. For example, the compounds of the invention may be labeled and used as probes for the detection and localization of C5a receptor (cell preparations or tissue sections samples). The compounds of the invention may also be used as positive controls in assays for C5a receptor activity, i.e., as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

The compounds provided herein may also be used within a variety of well-known cell separation methods. For example, modulators may be linked to the interior surface of a tissue culture plate or other support, for use as affinity ligands for immobilizing and thereby isolating, C5a receptors (e.g., isolating receptor-expressing cells) in vitro. In one preferred application, a modulator linked to a fluorescent marker, such as fluorescein, is contacted with the cells, which are then analyzed (or isolated) by fluorescence activated cell sorting (FACS).

V. EXAMPLES

The following examples are offered to illustrate, but not to limit the claimed invention.

Reagents and solvents used below can be obtained from commercial sources such as Aldrich Chemical Co. (Milwaukee, Wisconsin, USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M-H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM $NH_4OAc$ in acetonitrile/water as delivery system.

The following abbreviations are used in the Examples and throughout the description of the disclosure: mL, milliliters; mmol, millimoles; EtOH, ethanol; EtOAc, ethyl acetate; EtONa, sodium ethoxide; THF, tetrahydrofuran; TLC, thin layer chromatography; MeOH, methanol.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Some starting materials and intermediates are prepared in accordance with methods provided in WO 2010/075257 and US 20160090357, which are incorporated herein by reference.

Intermediates

Synthesis of 2-fluoro-6-(methyl-$d_3$)-benzoyl chloride

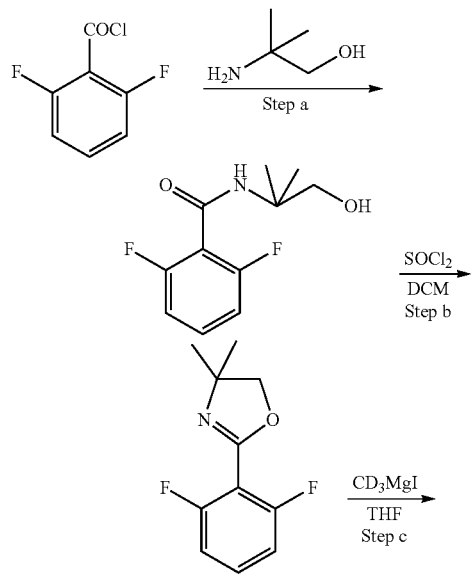

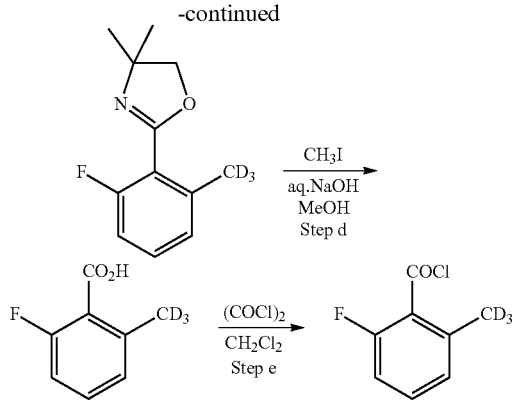

Step a: To a 0° C. solution of 2-amino-2-methyl-1-propanol (10.1 g, 113.3 mmol) in $CH_2Cl_2$ (75 mL) under nitrogen was added dropwise a solution of 2,6-difluorobenzoyl chloride (10.0 g, 56.6 mmol) in $CH_2Cl_2$ (50 mL). The reaction mixture was then warmed to room temperature and stirred for 16 h. The reaction mixture was diluted with $H_2O$, and the aqueous phase was extracted with $CH_2Cl_2$, dried over $Na_2SO_4$, and concentrated. The residue was purified by trituration with hexanes to give 2,6-difluoro-N-(1-hydroxy-2-methylpropan-2-yl)-benzamide as a white solid.

Step b: To a stirred solution of 2,6-difluoro-N-(1-hydroxy-2-methylpropan-2-yl)benzamide (6.0 g, 26.2 mmol) in $CH_2Cl_2$ (30 mL) at 0° C. was added $SOCl_2$ (4.9 g, 41.9 mmol). The reaction mixture was allowed to warm to room temperature and stirred for 6 h. The reaction mixture was concentrated and the residue was triturated with diethyl ether. The filter cake was taken up in $H_2O$ and basified with 6N NaOH aqueous solution. The mixture was extracted with $CH_2Cl_2$. The organic phase was combined, dried over $Na_2SO_4$, and concentrated to give 2-(2,6-difluorophenyl)-4,5-dihydro-4,4-dimethyloxazole as a white solid.

Step c: To an ice-bath cooled solution of 2-(2,6-difluorophenyl)-4,5-dihydro-4,4-dimethyloxazole (1.5 g, 7.1 mmol) in anhydrous THF (30 mL) was added dropwise 1M solution of $CD_3MgI$ in THF (20.6 mL, 20.6 mmol). The reaction mixture was stirred at 0° C. for 1 h, then the ice bath was removed, and the reaction mixture was stirred for 24 h at room temperature. After completion of the reaction, the mixture was quenched with saturated $NH_4Cl$ and extracted with EtOAc. The organic layer was washed with $H_2O$, brine, and dried over $Na_2SO_4$. The solution was filtered and concentrated in vacuo. The residue was purified by silica gel chromatography (0 to 50% EtOAc in hexanes) to give 2-(2-fluoro-6-(methyl-$d_3$)-phenyl)-4,4-dimethyl-4,5-dihydrooxazole as a white solid.

Step d: To a stirred solution of 2-(2-fluoro-6-(methyl-$d_3$)-phenyl)-4,4-dimethyl-4,5-dihydrooxazole (700 mg, 3.31 mmol) in acetonitrile (5 mL) was added methyl iodide (1.41 g, 9.93 mmol). The reaction mixture was heated to reflux for 6 h. The reaction mixture was stirred and allowed to cool to room temperature overnight. The reaction mixture was concentrated and the residue was triturated with diethyl ether and filtered. The solid was taken up in equal parts of 20% NaOH and methanol (5 mL) and heated to reflux for 6 h. The reaction mixture was cooled to room temperature, the organic solvent was removed in vacuo, and the aqueous phase was extracted with EtOAc to remove the byproducts. And then aqueous layer was acidified with 2N HCl (pH=1) and extracted with EtOAc. The organic layer was washed with brine, dried over $Na_2SO_4$, filtered and concentrated to give 2-fluoro-6-(methyl-d₃)-benzoic acid. ¹H NMR (400 MHz, CDCl₃) δ 7.25-7.37 (m, 1H), 7.03 (dd, J=0.8, 7.4 Hz, 1H), 6.96-7.02 (m, 1H). MS: (ES) m/z calculated for $C_8H_4FD_3O_2$ [M+H]⁺ 158.3, found 158.3.

Step e: To a 50 mL round bottom flask charged with 2-fluoro-6-(methyl-d₃)benzoic acid (0.45 g, 2.84 mmol) and anhydrous dichloromethane (15 mL) at 0° C. was added oxalyl chloride (0.72 g, 5.69 mmol) dropwise over 5 min. The reaction mixture was stirred at room temperature for 16 h. After completion of the reaction, the solvent was removed in vacuo to give 2-fluoro-6-methylbenzoyl chloride, which was used directly for the next step without further purification.

Synthesis of 2-fluoro-6-methylbenzoyl chloride-4-d

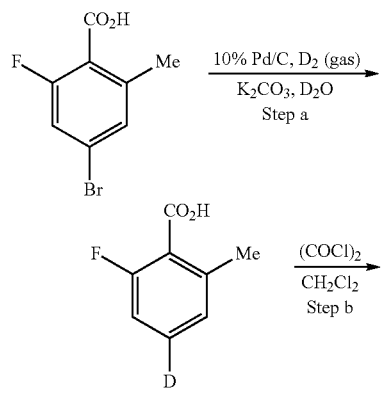

Step a: To a mixture of 4-bromo-2-fluoro-6-methylbenzoic acid (0.5 g, 2.14 mmol) and K₂CO₃ (0.35 g, 2.57 mmol) in D₂O (8 mL) was added 10% Pd-C (150 mg, prewashed in CD₃OD under deuterium gas) at room temperature. The resulting mixture was stirred under a deuterium gas atmosphere (balloon pressure) overnight. The reaction mixture was filtered through Celite and the aqueous filtrate was first extracted with Et₂O to remove the byproducts and then acidified with 2N HCl to pH 1. The aqueous layer was extracted with EtOAc, washed with brine, dried over Na₂SO₄, filtered and concentrated. The residue was dried under vacuum for 2 h to give 2-fluoro-6-(methylbenzoic-4-d) acid. ¹H NMR (400 MHz, CDCl₃) δ 7.04 (br, s, 1H), 6.97 (d, J=9.8 Hz, 1H), 2.4 (s, 3H). MS: (ES) m/z calculated for $C_8H_6DFO_2$ [M+H]⁺ 156.1, found 156.1

Step b: To a 50 mL round bottom flask charged with 2-fluoro-6-(methylbenzoic-4-d) acid (0.27 g, 1.73 mmol) and anhydrous dichloromethane (6 mL) at 0° C. was added oxalyl chloride (0.54 g, 4.32 mmol) dropwise over 5 min. The reaction mixture was stirred at room temperature for 16 h. After completion of the reaction, the solvent was removed under reduced pressure and the residue was dried under vacuum for 20 min to give 2-fluoro-6-methylbenzoyl chloride-4-d, which was used in Example 3 directly and without further purification.

Example 1: Synthesis of (2R,3S)-2-(4-(cyclopentylamino)phenyl)-1-(2-fluoro-6-(methyl-d₃)benzoyl)-N-(4-methyl-3-(trifluoromethyl)phenyl)piperidine-3-carboxamide

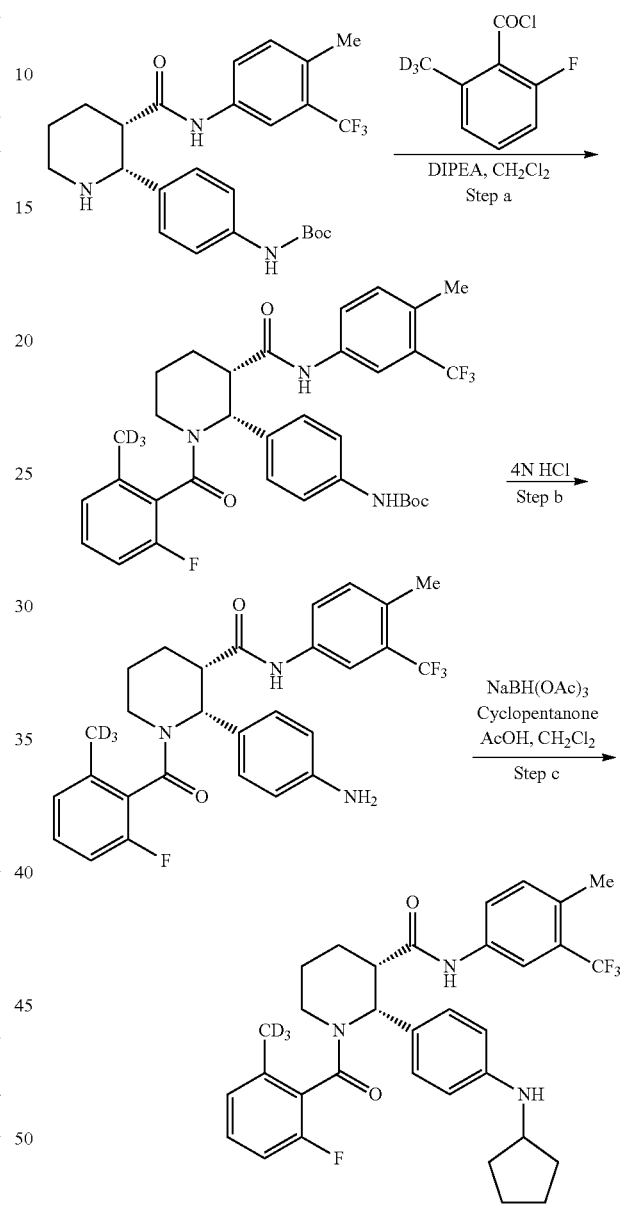

Step a: To a stirred solution of tert-butyl (4-((2R,3S)-3-((4-methyl-3-(trifluoromethyl)phenyl)carbamoyl)piperidin-2-yl)phenyl)carbamate (0.6 g, 1.25 mmol) and N,N-diisopropyl ethylamine (0.32 g, 2.51 mmol) in CH₂Cl₂ (10 mL) at −10° C., was added 2-fluoro-6-(methyl-d₃)benzoyl chloride (220 mg, 1.25 mmol) and the mixture was vigorously stirred for 2 h at room temperature. After completion, the reaction mixture was diluted with H₂O and extracted with CH₂Cl₂. The organic layers were combined, dried over Na₂SO₄, filtered, and concentrated. The residue was purified by silica gel column chromatography (10 to 60% EtOAc in hexanes) to give tert-butyl-(4-((2R,3S)-1-(2-fluoro-6-(methyl-d₃)benzoyl)-3((4-methyl-3-(trifluoromethyl)phenyl)carbamoyl)piperidin-2-yl)phenyl)carbamate. MS: (ES) m/z calculated for $C_{33}H_{32}D_3F_4N_3O_4$ [M+H]$^+$ 617.3, found 617.3.

Step b: To a stirred solution of tert-butyl-(4-((2R,3S)-1-(2-fluoro-6-(methyl-d$_3$)benzoyl)-3-((4-methyl-3-(trifluoromethyl)phenyl)carbamoyl)piperidin-2-yl)phenyl)carbamate (0.40 g, 0.64 mmol) in CH$_2$Cl$_2$ (8 mL) was added 4N HCl in dioxane (2.5 mL, 2.58 mmol). The reaction mixture was stirred at room temperature for 3 h. After completion, the reaction mixture was diluted with CH$_2$Cl$_2$. The organic layer was washed with saturated NaHCO$_3$, dried over Na$_2$SO$_4$, filtered, and concentrated. The residue was purified by silica gel flash chromatography (0-100% EtOAc in hexanes) to give (2R,3S)-2-(4-aminophenyl)-1-(2-fluoro-6-methyl-d$_3$)-benzoyl)-N-(4-methyl-3-(trifluoromethyl)-phenyl)-piperidine-3-carboxamide. MS: (ES) m/z calculated for $C_{28}H_{24}D_3F_4N_3O_2$ [M+H]$^+$ 517.2, found 517.2.

Step c: A mixture of (2R,3S)-2-(4-aminophenyl)-1-(2-fluoro-6-methylbenzoyl)-N-(4-methyl-3-(trifluoromethyl)-phenyl)piperidine-3-carboxamide (150 mg, 0.29 mmol), cyclopentanone (73 mg, 0.87 mmol), NaBH(OAc)$_3$ (183 mg, 0.72 mmol) and HOAc (17 mg, 0.29 mmol) in CH$_2$Cl$_2$ (4 mL) was stirred for 6 h at room temperature. The mixture was then basicified with saturated NaHCO$_3$ and extracted with CH$_2$Cl$_2$. The combined oranic layers were washed brine, dried over Na$_2$SO$_4$, filtered, and concentrated. The residue was purifed by silica gel flash chromatography (0 to 60% EtOAc in hexanes) to afford (2R,3S)-2-(4-(cyclopentylamino)phenyl)-1-(2-fluoro-6-(methyl-d$_3$)-benzoyl)-N-(4-methyl-3-(trifluoromethyl)phenyl)piperidine-3-carboxamide. MS: (ES) m/z calculated for $C_{33}H_{32}D_3F_4N_3O_2$ [M+H]$^+$ 585.3, found 585.2.

Example 2: Synthesis of (2R,3S)-2-(4-((cyclopentyl-3,3,4,4-d$_4$)amino)phenyl)-1-(2-fluoro-6-(methyl-d$_3$)benzoyl)-N-(4-methyl-3-(trifluoromethyl)phenyl)piperidine-3-carboxamide

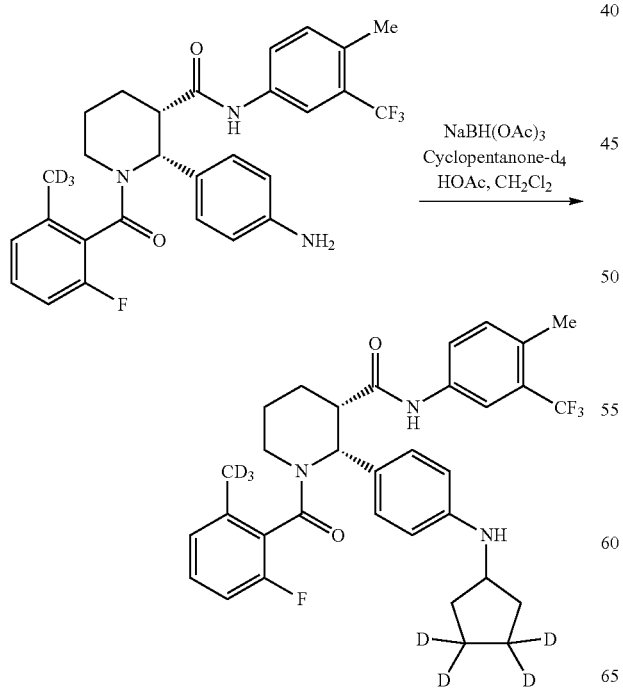

The title compound was prepared similar to the procedure as described in Example 1 using cyclopentanone-d$_4$ and (2R,3S)-2-(4-aminophenyl)-1-(2-fluoro-6-methyl-d$_3$)-benzoyl)-N-(4-methyl-3-(trifluoromethyl)-phenyl)-piperidine-3-carboxamide. MS: (ES) m/z calculated for $C_{33}H_{28}D_7F_4N_3O_2$ [M+H]$^+$ 589.3, found 589.2.

Example 3: Synthesis of (2R,3S)-2-(4-(cyclopentylamino)-phenyl)-1-(2-fluoro-6-methylbenzoyl-4-d)-N-(4-methyl-3-(trifluoromethyl)-phenyl)-piperidine-3-carboxamide

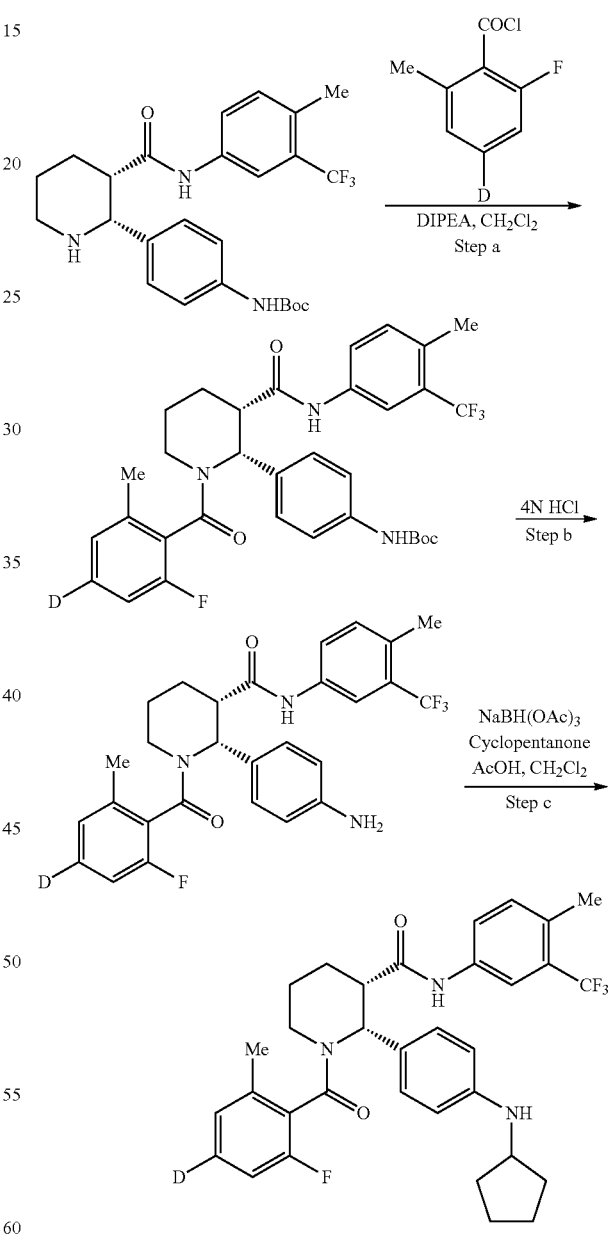

Step a: To a stirred solution of tert-butyl-(4-((2R,3S)-3-((4-methyl-3-(trifluoromethyl)phenyl)-carbamoyl)piperidin-2-yl)-phenyl)carbamate (0.4 g, 0.83 mmo) and N,N-diisopropyl ethylamine (0.21 g, 1.67 mmol) in CH$_2$Cl$_2$ (8 mL) at −10° C., was added 2-fluoro-6-methylbenzoyl chloride-4-d (0.17 g, 1.00 mmol). The mixture was vigorously stirred for 3 h at room temperature. After completion, the reaction mixture was diluted with H₂O and extracted with CH₂Cl₂. The combined organic layers were dried over Na₂SO₄, filtered, and concentrated. The residue was purified by silica gel column chromatography (10 to 50% EtOAc in hexanes) to give tert-butyl (4-((2R,3S)-1-(2-fluoro-6-methylbenzoyl-4-d)-3-((4-methyl-3-(trifluoromethyl)phenyl)carbamoyl)piperidin-2-yl)phenyl)carbamate. MS: (ES) m/z calculated for $C_{33}H_{34}DF_4N_3O_4$ [M+H]⁺, found 615.3.

Step b: To a stirred solution of tert-butyl (4-((2R,3S)-1-(2-fluoro-6-methylbenzoyl-4-d)-3-((4-methyl-3-(trifluoromethyl)phenyl)carbamoyl)piperidin-2-yl)phenyl)carbamate (0.45 g, 0.65 mmol) in CH₂Cl₂ (5 mL) was added 4N HCl in Dioxane (0.65 mL, 2.60 mmol). The reaction mixture was stirred at room temperature for 3 h and then diluted with CH₂Cl₂. The organic layer was washed with saturated NaHCO₃, dried over Na₂SO₄, filtered, and concentrated. The residue was purified by silica gel chromatography (0 to 100% EtOAc in hexanes) to give (2R,3S)-2-(4-aminophenyl)-1-(2-fluoro-6-methylbenzoyl-4-d)-N-(4-methyl-3-(trifluoromethyl)-phenyl)-piperidine-3-carboxamide. MS: (ES) m/z calculated for $C_{28}H_{26}DF_4N_3O_2$ [M+H]⁺ 515.2, found 515.3.

Step c: A mixture of (2R,3S)-2-(4-aminophenyl)-1-(2-fluoro-6-methylbenzoyl-4-d)-N-(4-methyl-3-(trifluoromethyl)phenyl)piperidine-3-carboxamide (150 mg, 0.29 mmol), cyclopentanone (73 mg, 0.87 mmol), NaBH(OAc)₃ (153 mg, 0.725 mmol) and HOAc (17 mg, 21.2 mmol) in CH₂Cl₂ (5 mL) was stirred for 5 h at room temperature. The mixture was then basicified with satuatred NaHCO₃ and extracted with CH₂Cl₂. The organic layer was washed with brine, dried over Na₂SO₄, filtered, and concentrated. The residue was purifed by silica gel flash chromatography (0 to 100% EtOAc in hexanes) to give (2R,3S)-2-(4-(cyclopentylamino)phenyl)-1-(2-fluoro-6-methylbenzoyl-4-d)-N-(4-methyl-3-(trifluoromethyl)-phenyl)piperidine-3-carboxamide. MS: (ES) m/z calculated for $C_{33}H_{34}DF_4N_3O_2$ [M+H]⁺ 583.3, found 583.2.

Example 4: Synthesis of (2R,3S)-2-(4-((cyclopentyl-3,3,4,4-d₄)amino)phenyl)-1-(2-fluoro-6-methylbenzoyl-4-d)-N-(4-methyl-3-(trifluoromethyl)phenyl)piperidine-3-carboxamide

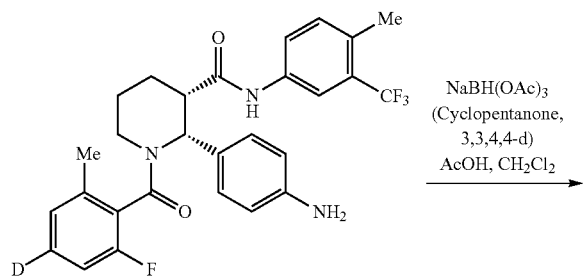

NaBH(OAc)₃
(Cyclopentanone, 3,3,4,4-d)
AcOH, CH₂Cl₂

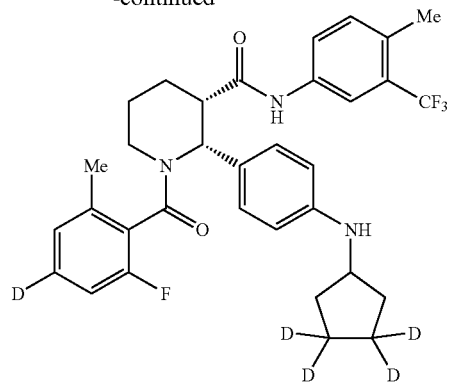

The title compound was prepared similar to the procedure as described in Example 3 using cyclopentanone-d₄, and (2R,3S)-2-(4-aminophenyl)-1-(2-fluoro-6-methylbenzoyl-4-d)-N-(4-methyl-3-(trifluoromethyl)phenyl)-piperidine-3-carboxamide. MS: (ES) m/z calculated for $C_{33}H_{30}D_5F_4N_3O_2$ [M+H]⁺ 587.3, found 587.3.

Example 5: Synthesis of (2R,3S)-2-(4-((cyclopentyl-1-d)-amino)-phenyl)-1-(2-fluoro-6-methylbenzoyl)-N-(4-methyl-3-(trifluoromethyl)-phenyl)-piperidine-3-carboxamide

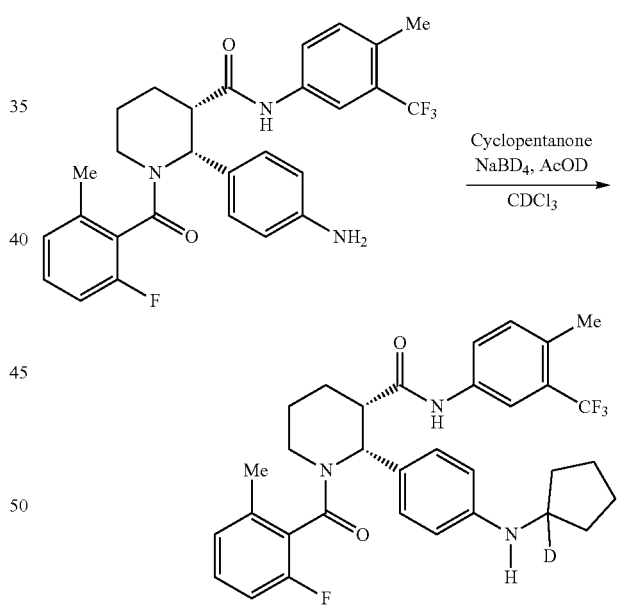

To a mixture of (2R,3S)-2-(4-aminophenyl)-1-(2-fluoro-6-methylbenzoyl)-N-(4-methyl-3-(trifluoromethyl)phenyl)piperidine-3-carboxamide (125 mg, 0.24 mmol), cyclopentanone (121 mg, 0.73 mmol) in CDCl₃ (120 mL) was added NaBD₄ (60 mg, 0.72 mmol) and AcOD (50 mg, 0.243 mmol). The nixture was stirred for 16 h at room temperature. The mixture was then basicified with saturated NaHCO₃ and extracted with CH₂Cl₂. The organic layer was separated, washed brine (50 mL), dried over anhydrous Na₂SO₄, filtered and concentrated. The residue was purified by reverse phase HPLC (MeCN/H₂O, with 0.1% TFA) to give (2R,3S)-2-(4-((cyclopentyl-1-d)amino)phenyl)-1-(2-fluoro- 6-methylbenzoyl)-N-(4-methyl-3-(trifluoromethyl)phenyl) piperidine-3-carboxamide. MS: (ES) m/z calculated for $C_{33}H_{34}DF_4N_3O_2$ [M+H]$^+$ 583.3, found 583.2.

Example 6: Synthesis of (2R,3S)-2-(4-(cyclopentylamino)phenyl)-1-(2-fluoro-6-methylbenzoyl)-N-(4-(hydroxymethyl-d$_2$)-3-(trifluoromethyl)phenyl)-piperidine-3-carboxamide

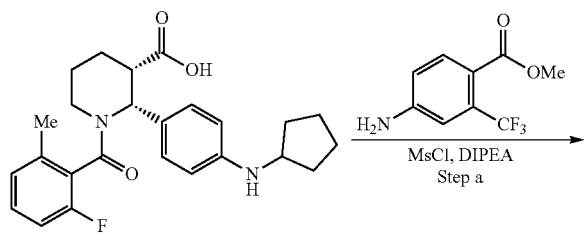

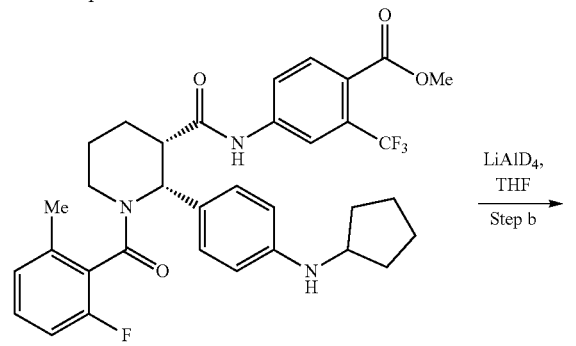

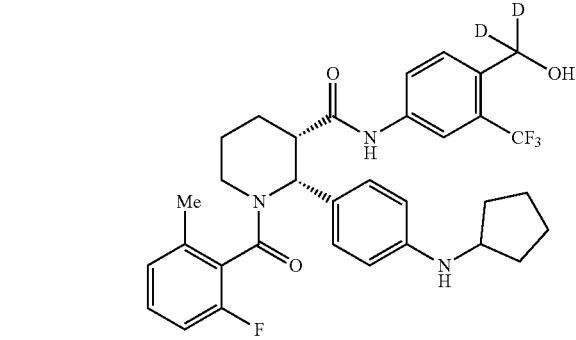

Step a: To a flask containing (2R,3S)-2-(4-(cyclopentylamino)phenyl)-1-(2-fluoro-6-methylbenzoyl)piperidine-3-carboxylic acid (250 mg, 0.58 mmol) in 8 mL of CH$_2$Cl$_2$ were added N,N-diisopropylethylamine (120 mg, 0.93 mmol) and methanesulfonyl chloride (1.1 mL, 0.69 mmol). After stirring for 1 h at 0° C., methyl-3-(trifluoromethyl) aniline (192 mg, 0.87 mmol) in CH$_2$Cl$_2$ (2 mL) was added. The reaction mixture was stirred for 2 h at room temperature. The reaction mixture was quenched with H$_2$O, and extracted with CH$_2$Cl$_2$. The combined organic layers were dried over Na$_2$SO$_4$, filtered, and concentrated. The residue was purified by silica gel column chromatography (10 to 60% EtOAc in hexanes) to give methyl 4-((2R,3S)-2-(4-(cyclopentylamino)phenyl)-1-(2-fluoro-6-methylbenzoyl) piperidine-3-carboxamido)-2-(trifluoromethyl)benzoate. MS: (ES) m/z calculated for $C_{34}H_{35}F_4N_3O_4$ [M+H]$^+$ 626.3, found: 626.3.

Step b: To a flask containing LiAlD$_4$ (28 mg, 0.67 mmol) was added anhydrous THF (4 mL) at 0° C. and the contents were stirred at 0° C. for 5 min. A solution of methyl 4-((2R,3S)-2-(4-(cyclopentylamino)phenyl)-1-(2-fluoro-6-methylbenzoyl)piperidine-3-carboxamido)-2-(trifluoromethyl)benzoate (140 mg, 0.22 mmol) in THF (2 mL) was added to the flask slowly, maintaining the temperature between 0-5° C. The reaction mixture was stirred for 1 h at 0° C. and quenched with dropwise addition of aqueous NaOH solution. The mixture was stirred for 10 minutes and extracted with EtOAc. The combined organic layers were dried over Na$_2$SO$_4$, filtered, and concentrated. The residue was purified by HPLC (MeCN/H$_2$O, with 0.1% TFA) to give (2R,3S)-2-(4-(cyclopentylamino)phenyl)-1-(2-fluoro-6-methylbenzoyl)-N-(4-(hydroxymethyl-d$_2$)-3-(trifluoromethyl)phenyl)piperidine-3-carboxamide. MS: (ES) m/z calculated for $C_{33}H_{33}D_2F_4N_3O_3$ [M+H]$^+$ 600.3, found 600.2.

Example 7: Synthesis of (2R,3S)-2-(4-(cyclopentylamino)phenyl)-1-(2-fluoro-6-methylbenzoyl)-N-(4-(methyl-d$_3$)-3-(trifluoromethyl)phenyl)piperidine-3-carboxamide

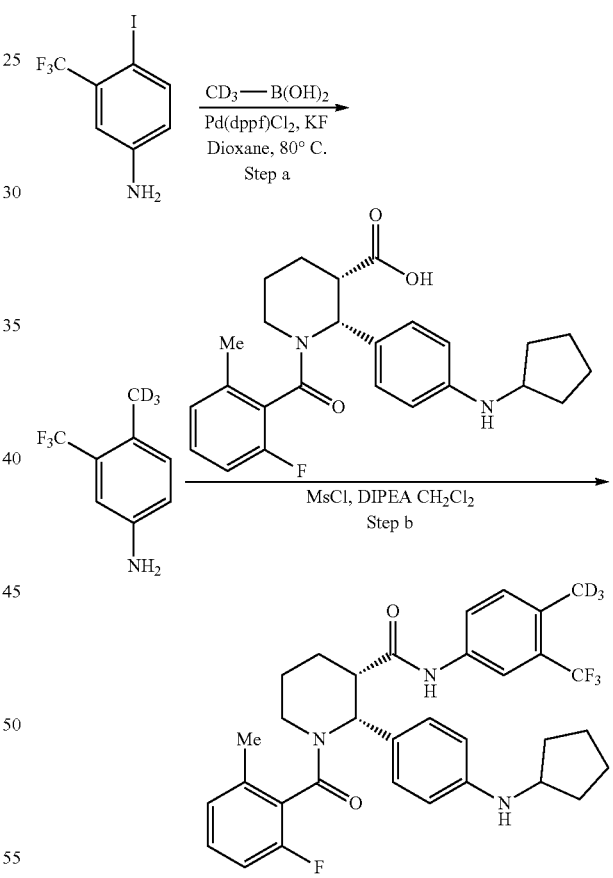

Step a: To a suspension of 3-(trifluoromethyl)-4-iodobenzenamine (180 mg, 0.62 mmol), (methyl-d$_3$) boronic acid (120 mg 1.88 mmol), and CsF (150 mg, 1.56 mmol) in dioxane (3 ml) was added Pd(dppf)Cl$_2$ complex with dichloromethane (52 mg, 0.062 mmol). The reaction mixture was degassed (N$_2$) for 2 min and stirred at 80° C. for 48 h. The reaction mixture was diluted with EtOAc, filtered through celite, washed with brine, and dried over Na$_2$SO$_4$. The solvent was removed under reduced pressure and the residue was purified by silica gel flash chromatography (0 to 20%

EtOAc in hexane) to give 4-(methyl-d₃)-3-(trifluoromethyl)aniline. MS: (ES) m/z calculated for $C_8H_5D_3F_3N$ [M+H]⁺ 179.1, found 179.1.

Step b: To a stirred solution of (2R,3S)-2-(4-(cyclopentylamino)phenyl)-1-(2-fluoro-6-methylbenzoyl)piperidine-3-carboxylic acid (100 mg, 0.23 mmol) in $CH_2Cl_2$ (5 mL) at 0° C., was added N,N-diisopropylethylamine (48 mg, 0.37 mmol) and methanesulfonylchloride (34 mg, 0.29 mmol). The reaction mixture was stirred for 45 minutes at 0° C. and then 4-(methyl-d₃)-3-(trifluoromethyl)aniline (52 mg, 0.29 mmol) in $CH_2Cl_2$ (2 mL) was added and stirred for another 2 h at room temperature. The reaction mixture was quenched with dropwise addition of saturated $NaHCO_3$ and extracted with $CH_2Cl_2$. The organic layer was washed with brine, dried over $Na_2SO_4$, filtered and concentrated. The residue was purified by silica gel flash chromatography (0 to 50% EtOAc in hexanes) to yield (2R,3S)-2-(4-(cyclopentylamino)phenyl)-1-(2-fluoro-6-methylbenzoyl)-N-(4-(methyl-d₃)-3-(trifluoromethyl)phenyl)piperidine-3-carboxamide. MS: (ES) m/z calculated for $C_{33}H_{32}D_3F_4N_3O_2$ [M+H]⁺ 585.3, found 585.3.

Example 8: Synthesis of (2R,3S)-2-(4-(cyclopentylamino)phenyl)-1-(2-fluoro-6-(methyl-d₃)benzoyl)-N-(4-methyl-3-(trifluoromethyl)phenyl-2,6-d₂)piperidine-3-carboxamide

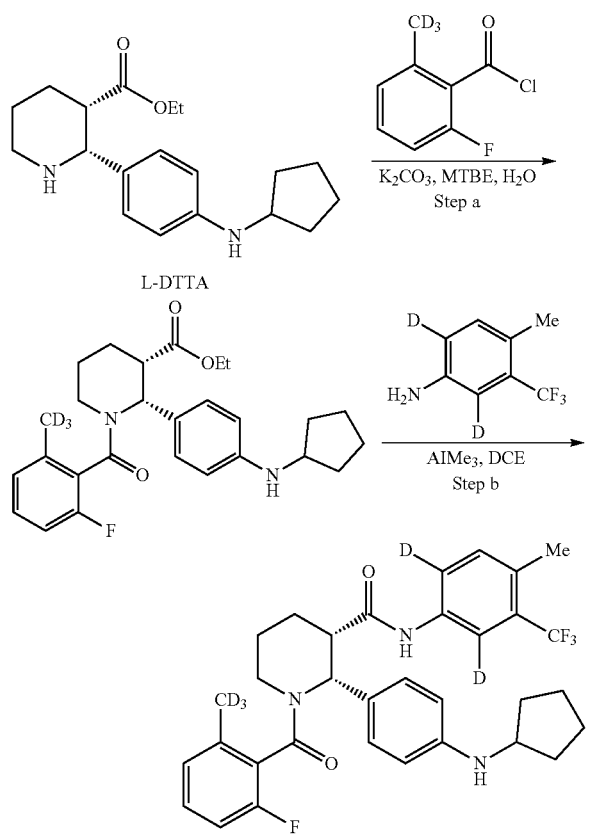

Step a: To a vial containing a solution of the L-DTTA salt of ethyl (2R,3S)-2-(4-(cyclopentylamino)phenyl)piperidine-3-carboxylate (9.12 g, 8.4 mmol) in MTBE (14.6 mL) was added a solution of potassium carbonate (3.65 g, 26.4 mmol) in $H_2O$ (14.6 mL), followed by 2-fluoro-6-(methyl-d₃)benzoyl chloride (1.46 g, 8.4 mmol). The mixture was stirred at room temperature for 3 h. Upon completion, the mixture was extracted with EtOAc. The combined organic phases were dried over $Na_2SO_4$, filtered, and concentrated. The residue was purified by silica gel column chromatography (40% EtOAc in Hexanes) to afford ethyl (2R,3S)-2-(4-(cyclopentylamino)phenyl)-1-(2-fluoro-6-(methyl-d₃)benzoyl)piperidine-3-carboxylate.

Step b: To a flask containing ethyl (2R,3S)-2-(4-(cyclopentylamino)phenyl)-1-(2-fluoro-6-(methyl-d₃)benzoyl)piperidine-3-carboxylate (100 mg, 0.22 mmol) in DCE (1 mL) was added 4-methyl-3-(trifluoromethyl)benzen-2,6-d₂-amine (70 mg, 0.39 mmol) followed by a solution of 2M $AlMe_3$ (0.39 mL, 0.78 mmol). The contents were heated at 65° C. for 2 h. The reaction was quenched by the slow addition of aqueous NaOH solution. The mixture was filtered and the solids were washed with $CH_2Cl_2$. The organic layer was separated and the aqueous layer was extracted with EtOAc. The combined organic layers were dried over $Na_2SO_4$, filtered, and concentrated. The crude residue was purified by silica gel column chromatography (40% EtOAc in hexanes), followed by HPLC to yield (2R,3S)-2-(4-(cyclopentylamino)phenyl)-1-(2-fluoro-6-(methyl-d₃)benzoyl)-N-(4-methyl-3-(trifluoromethyl)phenyl-2,6-d₂)piperidine-3-carboxamide. MS: (ES) m/z calculated for $C_{33}H_{30}D_5F_4N_3O_2$ [M+H]⁺ 587.3, found 587.3.

Example 9: Synthesis of (2R,3S)-2-(4-(cyclopentylamino)phenyl)-1-(2-fluoro-6-(methyl-d₃)benzoyl)-N-(4-(methyl-d₃)-3-(trifluoromethyl)phenyl)piperidine-3-carboxamide

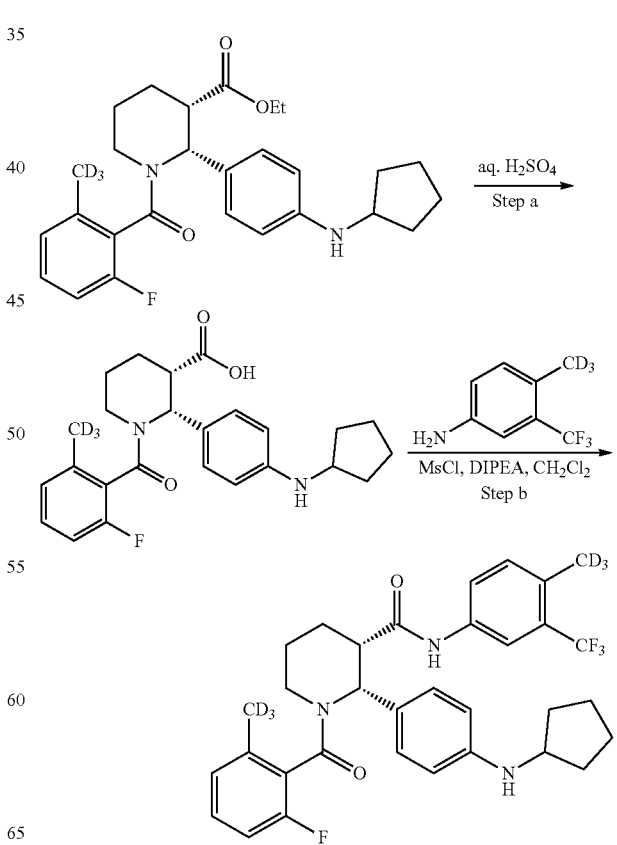

Step a: Ethyl (2R,3S)-2-(4-(cyclopentylamino)phenyl)-1-(2-fluoro-6-(methyl-d₃)benzoyl)piperidine-3-carboxylate (175 mg, 0.384 mmol) was added portionwise to a flask containing 5 mL of aqueous 1M H$_2$SO$_4$ at 70° C. An additional 2 mL of 1M H$_2$SO$_4$ was used to wash the solids down from the funnel. The suspension was heated to 85° C. and stirred at this temperature for 16 h. The reaction was cooled to ambient temperature. To the mixture was added 3 mL of aqueous 1.7 M NaOH, followed by 20 mL of MTBE and 2 mL of aqueous 1.7 M NaOH. The mixture was vigorously stirred until all the solids dissolved. The mixture was extracted with MTBE. The organic layer was concentrated in vacuo to to give (2R,3S)-2-(4-(cyclopentylamino)phenyl)-1-(2-fluoro-6-(methyl-d₃)benzoyl)piperidine-3-carboxylic acid. MS: (ES) m/z calculated for C$_{25}$H$_{26}$D$_3$FN$_2$O$_3$ [M+H]⁺ 428.2, found 428.3.

Step b: The title compound was prepared similar to the procedure as described in Example 7 using (2R,3S)-2-(4-(cyclopentylamino)phenyl)-1-(2-fluoro-6-(methyl-d₃)benzoyl)piperidine-3-carboxylic acid and 4-(methyl-d₃)-3-(trifluoromethyl)-aniline. MS: (ES) m/z calculated for C$_{33}$H$_{29}$D$_6$F$_4$N$_3$O$_2$ [M+H]⁺ 588.3, found 588.3.

Example 10: Synthesis of (2R,3S)-2-(4-(cyclopentylamino)phenyl)-1-(2-fluoro-6-(methyl-d₃)benzoyl)-N-(4-(hydroxymethyl-d₂)-3-(trifluoromethyl)phenyl)piperidine-3-carboxamide

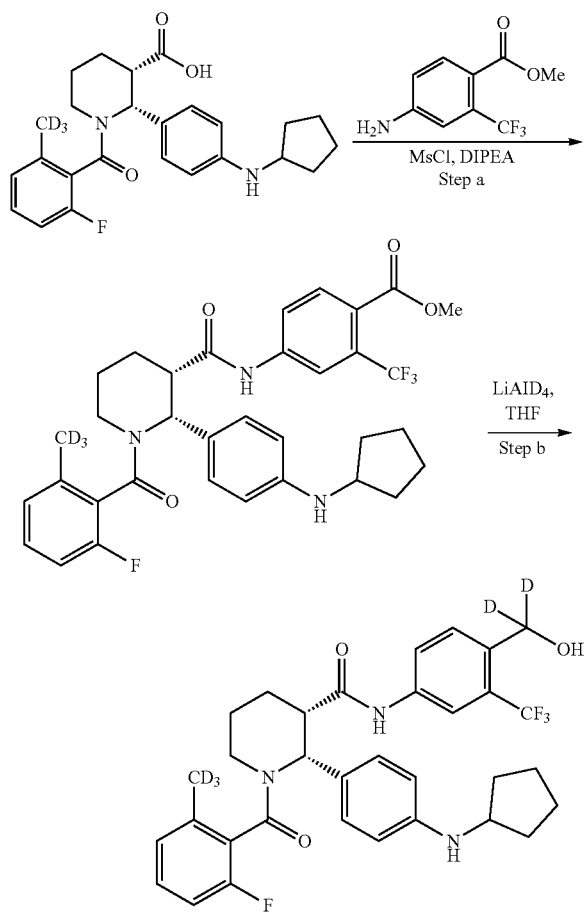

The title compound was prepared similar to the procedure as described in Example 6 using (2R,3S)-2-(4-(cyclopentylamino)phenyl)-1-(2-fluoro-6-(methyl-d₃)benzoyl)piperidine-3-carboxylic acid and methyl 4-amino-2-(trifluoromethyl)benzoate. MS: (ES) m/z calculated for C$_{33}$H$_{30}$D$_5$F$_4$N$_3$O$_3$ [M+H]⁺ 603.3, found 603.3.

Example 11: Synthesis of (2R,3S)-2-(4-(cyclopentylamino)phenyl)-1-(2-fluoro-6-(methyl-d₃)benzoyl)-N-(4-(hydroxymethyl)-3-(trifluoromethyl)phenyl)piperidine-3-carboxamide

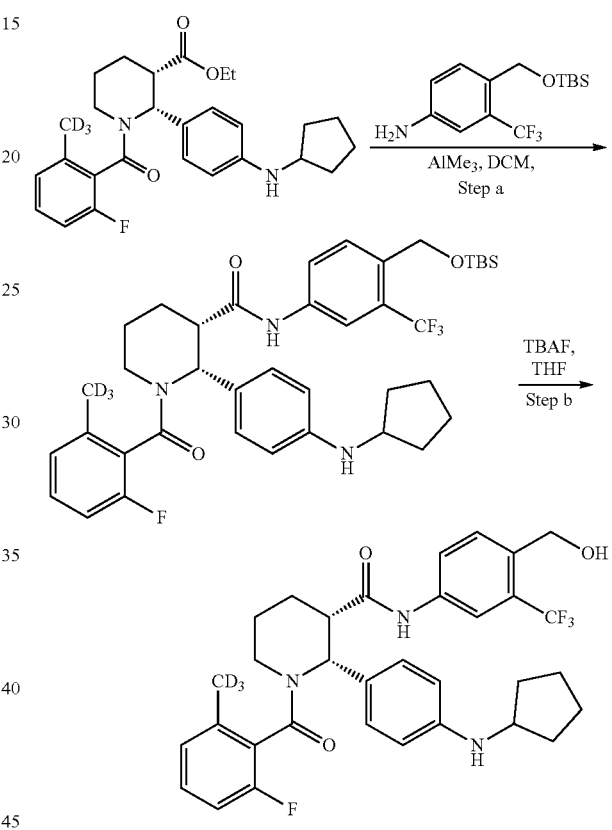

Step a: A solution of 2M AlMe$_3$ in toluene (0.48 mL, 0.98 mmo) was added slowly to a stirred solution of ethyl (2R,3S)-2-(4-(cyclopentylamino)phenyl)-1-(2-fluoro-6-(methyl-d₃)benzoyl)piperidine-3-carboxylate (150 mg, 0.32 mmol) and (4-amino-2-(trifluoromethyl)phenyl)methanol (120 mg, 0.39 mmol) in CH$_2$Cl$_2$ (5 mL) at ambient temperature. The mixture was heated between 35-45° C. for 30 h. After cooling to room temperature, 1N aqueous NaOH solution was added slowly, maintaining the temperature between 15-35° C. The mixture was filtered and the solid was washed with CH$_2$Cl$_2$. The organic layer of the filtrate was separated, and dried over Na$_2$SO$_4$ and filtered. The solvent was removed under reduced pressure and the residue was dried under vacuum for 30 min and used directly for the next step without further purification.

Step b: To the above crude compound in anhydrous THF (5 mL) was added 1M TBAF solution in THF (1.0 mL, 1 mmol). The resultant mixture was stirred for 2 h at room temperature and quenched with H$_2$O. The mixture was extracted with EtOAc. The organic layer was washed with brine, dried over Na$_2$SO$_4$, and filtered. The solvent was removed under reduced pressure. The residue was purified by HPLC (MeCN/H₂O, with 0.1% TFA) to give (2R,3S)-2-(4-(cyclopentylamino)phenyl)-1-(2-fluoro-6-(methyl-d₃)benzoyl)-N-(4-(hydroxymethyl)-3-(trifluoromethyl)phenyl)piperidine-3-carboxamide. MS: (ES) m/z calculated for $C_{33}H_{32}D_3F_4N_3O_3$ [M+H]⁺ 601.3, found 601.2.

Example 12: Synthesis of (2R,3S)-2-(4-(cyclopentylamino)-phenyl)-1-(2-fluoro-6-methylbenzoyl-4-d)-N-(4-(hydroxymethyl-d₂)-3-(trifluoromethyl)-phenyl)-piperidine-3-carboxamide

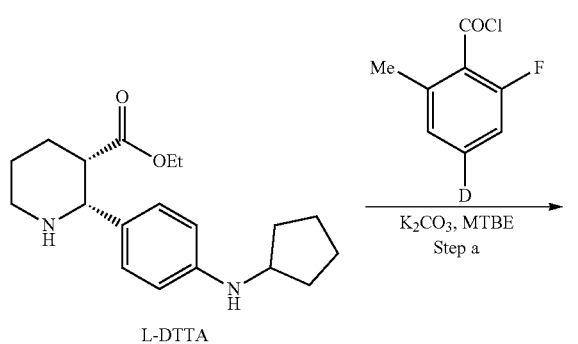

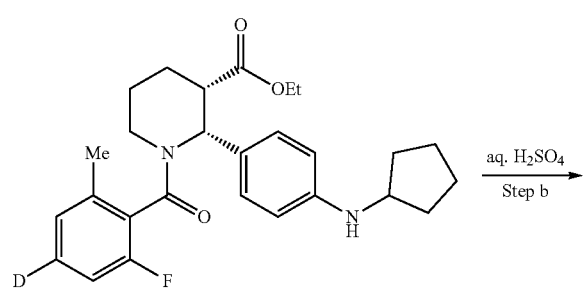

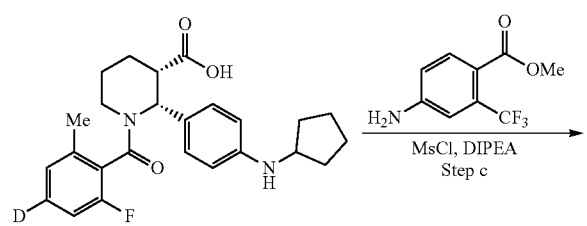

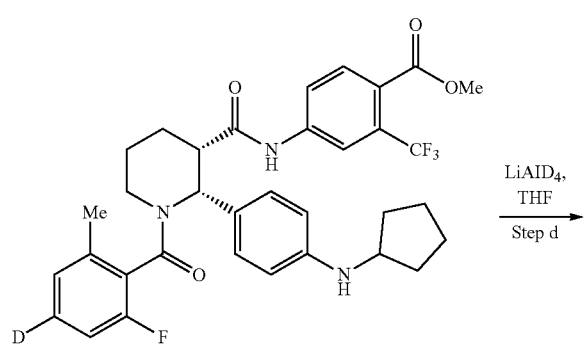

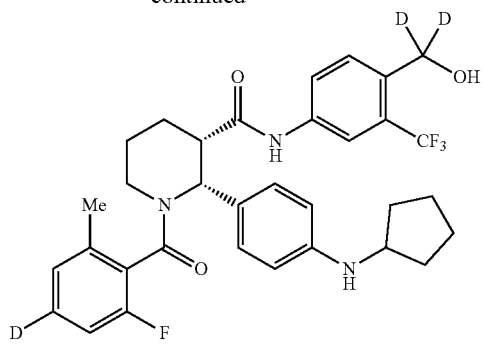

Step a: To a 100 mL flask containing 8 mL of water and potassium carbonate (0.76 g, 1.37 mmol) was added slowly ethyl (2R,3S)-2-(4-((tert-butoxycarbonyl)amino)phenyl)-piperidine-3-carboxylate L-DTTA salt (1.5 g, 1.37 mmol), followed by 40 mL of MTBE. The contents were stirred between 15-25° C. until a solution is formed, then 2-fluoro-6-methylbenzoyl chloride-4-d (265 mg, 1.51 mmol) was added and the contents were vigorously stirred for 3 h at 20° C. The mixture was extracted with MTBE, dried over Na₂SO₄, filtered and concentrated in vacuo. The residue was purified by silica gel column chromatography (5 to 60% EtOAc in hexanes) to give ethyl (2R,3S)-2-(4-((tert-butoxycarbonyl)-amino)-phenyl)-1-(2-fluoro-6-methylbenzoyl)-piperidine-3-carboxylate. MS: (ES) m/z calculated for $C_{27}H_{32}DFN_2O_3$ [M+H]⁺ 10 453.3, found: 453.3.

Step b: (2R,3S)-2-(4-(cyclopentylamino)phenyl)-1-(2-fluoro-6-methylbenzoyl-4-d)piperidine-3-carboxylic acid was prepared similar to the procedure as described in Example 9. MS: (ES) m/z calculated for $C_{25}H_{28}DFN_2O_3$ [M+H]⁺ 426.2, found 426.2

Step c and d: (2R,3S)-2-(4-(cyclopentylamino)phenyl)-1-(2-fluoro-6-methylbenzoyl-4-d)-N-(4-(hydroxymethyl-d₂)-3-(trifluoromethyl)phenyl)piperidine-3-carboxamide was prepared similar to the procedure as described in Example 10. MS: (ES) m/z calculated for $C_{33}H_{33}D_3F_4N_3O_3$ [M+H]⁺ 600.3, found 600.2.

Example 13: Synthesis of (2R,3S)-2-(4-((cyclopentyl-d9)amino)phenyl)-1-(2-fluoro-6-methylbenzoyl)-N-(4-methyl-3-(trifluoromethyl)phenyl)piperidine-3-carboxamide

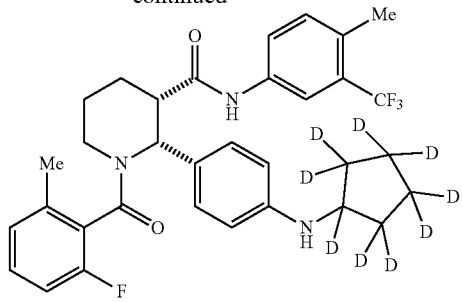

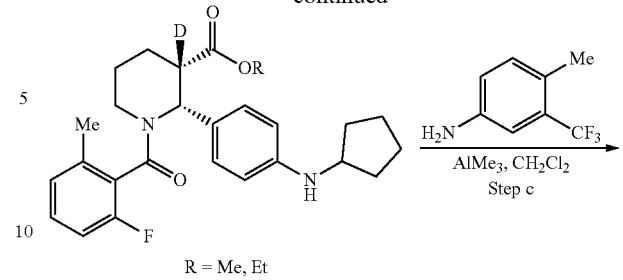

Step a: (2R,3S)-2-(4-aminophenyl)-1-(2-fluoro-6-methylbenzoyl)-N-(4-methyl-3-(trifluoromethyl)phenyl)piperidine-3-carboxamide was washed with CH₃OD and dried in vacuo prior to use. To a vial containing the pre-treated carboxamide (200 mg, 0.39 mmol) in 2.3 mL of CH$_2$Cl$_2$ was added cyclopentanone-d$_8$ (0.10 mL, 1.17 mmol) and acetic acid-$_4$ (0.02 mL, 0.39 mmol). The solution was stirred at room temperature for 15 min. In a separate vial, acetic acid-d$_4$ (0.24 mL, 4.19 mmol) was added to a solution containing NaBD$_4$ (59 mg, 1.41 mmol) in 1 mL of CH$_2$Cl$_2$. The mixture was stirred at ambient temperature for 30 min to form NaBD(OAc)$_3$. The slurry of the newly formed NaBD(OAc)$_3$ was added to the vial containing the carboxamide and cyclopentanone and the mixture was stirred at room temperature for 16 h. The reaction was quenched with D$_2$O and the aqueous layer was extracted with EtOAc. The combined organic layers were dried over Na$_2$SO$_4$, filtered, and concentrated in vacuo. The residue was purified by HPLC (MeCN/H$_2$O, with 0.1% TFA) to yield (2R,3S)-2-(4-((cyclopentyl-d$_9$)amino)phenyl)-1-(2-fluoro-6-methylbenzoyl)-N-(4-methyl-3-(trifluoromethyl)phenyl)piperidine-3-carboxamide (contains approximately 20% of the corresponding d$_8$ compound based on MS isotope). MS: (ES) m/z calculated for C$_{33}$H$_{26}$D$_9$F$_4$N$_3$O$_2$ [M+H]$^+$ 591.3, found 591.3.

Example 14: Synthesis of (2R,3S)-2-(4-(cyclopentylamino)phenyl)-1-(2-fluoro-6-methylbenzoyl)-N-(4-methyl-3-(trifluoromethyl)phenyl)piperidine-3-d-3-carboxamide

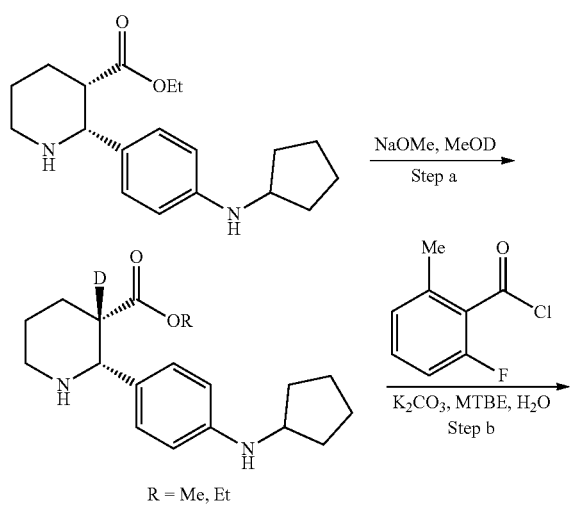

Step a: To a vial containing ethyl (2R,3S)-2-(4-(cyclopentylamino)phenyl)piperidine-3-carboxylate (250 mg, 0.79 mmol) in 20 mL of MeOD was added sodium methoxide (1.5 g, 27.8 mmol). The solution was stirred at 80° C. for 4 h then quenched with D$_2$O. The mixture was concentrated in vacuo to remove the organics and the remaining aqueous layer was extracted with EtOAc. The combined organic layers were dried over Na$_2$SO$_4$, filtered, and concentrated. The residue was purified by silica gel column chromatography to provide a mixture of methyl and ethyl (2R,3S)-2-(4-(cyclopentylamino)phenyl)piperidine-3-carboxylate-3-d as an oil.

Step b: To a vial containing a solution of a mixture of methyl and ethyl (2R,3S)-2-(4-(cyclopentylamino)phenyl)piperidine-3-carboxylate-3-d (244 mg, 0.77 mmol) in 1.6 mL of MTBE was added a solution of solid potassium carbonate (430 mg, 3.11 mmol) in 1.6 mL of H$_2$O followed by 2-fluoro-6-methylbenzoyl chloride (0.11 mL, 0.77 mmol). The contents were stirred for 1 h at room temperature. Upon completion, the mixture was extracted with EtOAc. The combined organic layers were dried over Na$_2$SO$_4$, filtered, and concentrated. The residue was purified by silica gel column chromatography to afford a mixture of methyl and ethyl (2R,3S)-2-(4-(cyclopentylamino)phenyl)-1-(2-fluoro-6-methylbenzoyl)piperidine-3-carboxylate-3-d.

Step c: To a flask containing a mixture of methyl and ethyl (2R,3S)-2-(4-(cyclopentylamino)phenyl)-1-(2-fluoro-6-methylbenzoyl)piperidine-3-carboxylate-3-d (128 mg, 0.28 mmol) in CH$_2$Cl$_2$ (0.6 mL) was added 4-methyl-3-(trifluoromethyl)aniline (0.05 mL, 0.34 mmol) followed by a solution of 2M AlMe$_3$ in toluene (0.42 mL, 0.85 mmol). The contents were heated at 40° C. for 20 h. The reaction was quenched by slow addition of aqueous NaOH. The mixture was filtered and the solids were washed with CH$_2$Cl$_2$. The organic layer was separated and the aqueous layer was extracted with EtOAc. The combined organic layers were dried over Na$_2$SO$_4$, filtered, and concentrated. The residue was purified by HPLC (MeCN/H$_2$O, with 0.1% TFA), followed by silica gel column chromatography (50% EtOAc in hexanes) to provide (2R,3S)-2-(4-(cyclopentylamino)phenyl)-1-(2-fluoro-6-methylbenzoyl)-N-(4-methyl-3-(trifluoromethyl)phenyl)piperidine-3-d-3-carboxamide (contains approximately 7% of trans isomer based on NMR). MS: (ES) m/z calculated for $C_{33}H_{34}DF_4N_3O_2$ [M+H]$^+$ 583.3, found 583.2.

Example 15: Synthesis of (2R,3S)-2-(4-(cyclopentylamino)phenyl-3-d)-1-(2-fluoro-6-methylbenzoyl)-N-(4-methyl-3-(trifluoromethyl)phenyl)piperidine-3-carboxamide

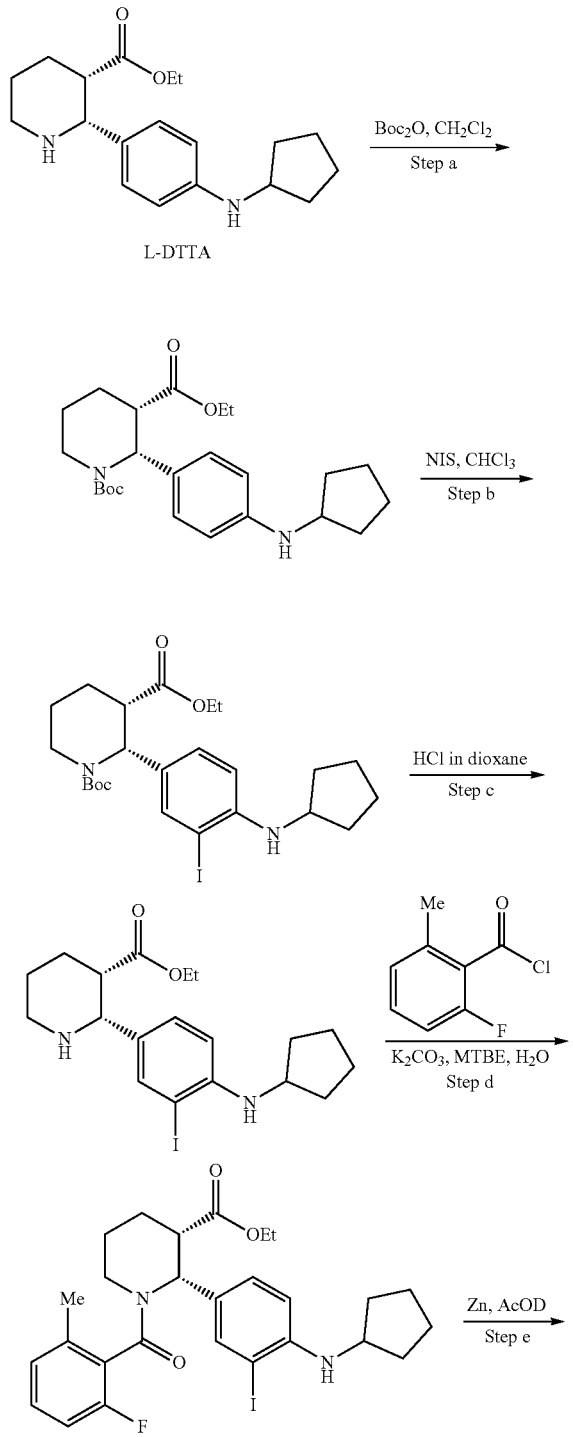

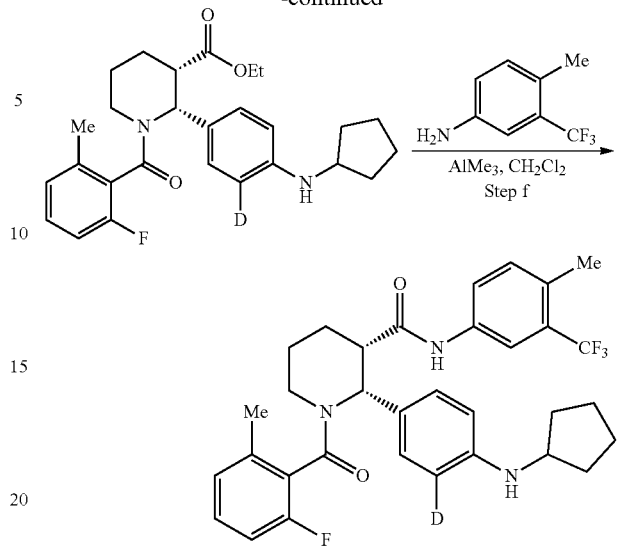

Step a: To a flask containing a solution of the L-DTTA salt of ethyl (2R,3S)-2-(4-(cyclopentylamino)phenyl)piperidine-3-carboxylate (17.2 g, 15.9 mmol) in 40 mL of EtOAc was added a solution of potassium carbonate (10.9 g, 79 mmol) in H$_2$O (40 mL). The mixture was stirred at room temperature for 30 min. The organic and aqueous layers were separated and the aqueous layer was extracted with EtOAc. The organic layers were combined, dried with Na$_2$SO$_4$, filtered and concentrated. The crude material was dissolved in 80 mL of CH$_2$Cl$_2$ and Boc anhydride (3.6 mL, 15.9 mmol) was added to the solution. The solution was stirred at room temperature for 2 h and then concentrated in vacuo. The residue was purified by silica gel column chromatography to yield 1-(tert-butyl) 3-ethyl (2R,3S)-2-(4-cyclopentylamino)-phenyl)piperidine-1,3-dicarboxylate.

Step b: To a flask containing 1-(tert-butyl) 3-ethyl (2R, 3S)-2-(4-(cyclopentylamino)phenyl)piperidine-1,3-dicarboxylate (5.55 g, 13.3 mmol) in 84 mL of CHCl$_3$ was added N-iodosuccinimide (2.99 g, 13.3 mmol). The solution was stirred at room temperature for 2 h and then concentrated in vacuo. The residue was purified by silica gel column chromatography to give 1-(tert-butyl) 3-ethyl (2R,3S)-2-(4-(cyclopentylamino)-3-iodophenyl)piperidine-1,3-dicarboxylate.

Step c: To a vial containing 1-(tert-butyl) 3-ethyl (2R, 3S)-2-(4-(cyclopentylamino)-3-iodophenyl)piperidine-1,3-dicarboxylate (500 mg, 0.92 mmol) in 5 mL of dioxane/H$_2$O (4:1) was added 0.92 mL of 4.0 N HCl in dioxane. The solution was stirred at 80° C. for 6 h and then slowly quenched with saturated NaHCO$_3$. The aqueous layer was extracted with EtOAc. The combined organic layers were dried over Na$_2$SO$_4$, filtered, and concentrated. The residue was purified by silica gel column chromatography to produce ethyl (2R,3S)-2-(4-(cyclopentylamino)-3-iodophenyl) piperidine-3-carboxylate.

Step d: To a vial containing a solution of ethyl (2R,3S)-2-(4-(cyclopentylamino)-3-iodophenyl)piperidine-3-carboxylate (130 mg, 0.29 mmol) in 1 mL of MTBE was added a solution of potassium carbonate (120 mg, 0.87 mmol) in 1 mL of H$_2$O followed by 2-fluoro-6-methylbenzoyl chloride (0.05 g, 0.29 mmol). The contents were stirred at room temperature for 30 min and the mixture was then extracted with EtOAc. The organic layers were combined, dried over Na$_2$SO$_4$, filtered, and concentrated. The residue was purified by silica gel column chromatography (30% EtOAc in Hexanes) to afford ethyl (2R,3S)-2-(4-(cyclopentylamino)-3-iodophenyl)-1-(2-fluoro-6-methylbenzoyl)piperidine-3-carboxylate.

Step e: To a vial containing (2R,3S)-2-(4-(cyclopentylamino)-3-iodophenyl)-1-(2-fluoro-6-methylbenzoyl)piperidine-3-carboxylate (125 mg, 0.22 mmol) in 2 mL of acetic acid-$d_4$ was added zinc powder (185 mg, 2.83 mmol). The mixture was stirred at room temperature for 5 h. The contents were filtered and the filtrate was concentrated. The residue was purified on silica gel column chromatography to yield ethyl (2R,3S)-2-(4-(cyclopentylamino)phenyl-3d)-1-(2-fluoro-6-methylbenzoyl)piperidine-3-carboxylate.

Step f: To a flask containing ethyl (2R,3S)-2-(4-(cyclopentylamino)phenyl-3-d)-1-(2-fluoro-6-methylbenzoyl)piperidine-3-carboxylate (80 mg, 0.18 mmol) in 1 mL of $CH_2Cl_2$ was added 4-methyl-3-(trifluoromethyl)aniline (31 mg, 0.21 mmol) followed by a solution of 2M $AlMe_3$ in toluene (0.26 mL, 0.52 mmol). The contents were heated at 40° C. for 20 h. The reaction was quenched by the slow addition of aqueous NaOH. The mixture was filtered and the solids were washed with $CH_2Cl_2$. The organic layer was separated and the aqueous layer was extracted with EtOAc. The combined organic layers were dried over $Na_2SO_4$, filtered, and concentrated. The residue was purified by HPLC (MeCN/$H_2O$, with 0.1% TFA), followed by silica gel column chromatography to provide (2R,3S)-2-(4-(cyclopentylamino)phenyl-3-d)-1-(2-fluoro-6-methylbenzoyl)-N-(4-methyl-3-(trifluoromethyl)phenyl)piperidine-3-carboxamide. MS: (ES) m/z calculated for $C_{33}H_{34}DF_4N_3O_2$ [M+H]$^+$ 583.3, found 583.2.

Example 16: Synthesis of (2R,3S)-2-(4-(cyclopentylamino)phenyl-3-d)-1-(2-fluoro-6-methylbenzoyl)-N-(4-methyl-3-(trifluoromethyl)phenyl)piperidine-3-carboxamide

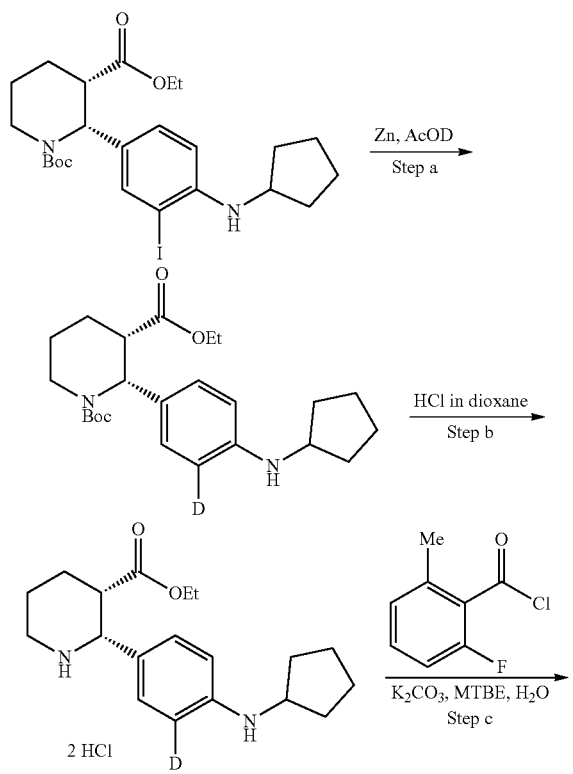

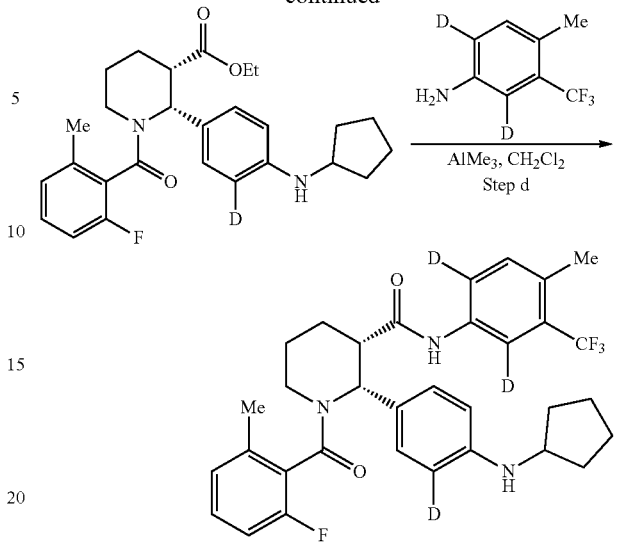

Step a: To a vial containing 1-(tert-butyl) 3-ethyl (2R,3S)-2-(4-(cyclopentylamino)-3-iodophenyl)piperidine-1,3-dicarboxylate (500 mg, 0.92 mmol) in acetic acid-di (9.2 mL) was added zinc powder (800 mg, 12.2 mmol). The mixture was stirred at room temperature for 30 min. The contents were filtered and the filtrate was concentrated. The residue was purified on silica gel column chromatography (40% EtOAc in hexanes) to yield 1-(tert-butyl) 3-ethyl (2R,3S)-2-(4-(cyclopentylamino)phenyl-3-d)piperidine-1,3-dicarboxylate.

Step b: To a vial containing 1-(tert-butyl) 3-ethyl (2R,3S)-2-(4-(cyclopentylamino)phenyl-3-d)piperidine-1,3-dicarboxylate (347 mg, 0.83 mmol) in 5 mL of dioxane/$H_2O$ (4:1) was added 0.83 mL of 4.0 N HCl in dioxane. The solution was stirred at room temperature for 16 h and then heated at 60° C. for 2 h. The solution was concentrated and the crude material was used without further purification.

Step c: To a vial containing a solution of the HCl salt of ethyl (2R,3S)-2-(4-(cyclopentylamino)phenyl-3-d)piperidine-3-carboxylate (150 mg, 0.39 mmol) in MTBE (1 mL) was added a solution of potassium carbonate (162 mg, 1.17 mmol) in $H_2O$ (1 mL) followed by 2-fluoro-6-methylbenzoyl chloride (67 mg, 0.39 mmol). The mixture was stirred at room temperature for 2 h then the mixture was extracted with EtOAc. The organic phases were combined, dried with $Na_2SO_4$, filtered and concentrated. The residue was purified by silica gel column chromatography (40% EtOAc in Hexanes) to afford ethyl (2R,3S)-2-(4-(cyclopentylamino)phenyl-3-d)-1-(2-fluoro-6-methylbenzoyl)piperidine-3-carboxylate.

Step d: To a flask containing ethyl (2R,3S)-2-(4-(cyclopentylamino)phenyl-3-d)-1-(2-fluoro-6-methylbenzoyl)piperidine-3-carboxylate (124 mg, 0.27 mmol) in $CH_2Cl_2$ (1 mL) was added 4-methyl-3-(trifluoromethyl)benzen-2,6-$d_2$-amine (49 mg, 0.33 mmol) followed by a solution of 2M $AlMe_3$ in toluene (0.42 mL, 0.84 mmol). The contents were heated at 40° C. for 20 h. The reaction was quenched by the slow addition of aqueous NaOH. The mixture was filtered and the solids were washed with $CH_2Cl_2$. The organic layer was separated and the aqueous layer was extracted with EtOAc. The combined organic layers were dried over $Na_2SO_4$, filtered, and concentrated. The residue was purified by HPLC (MeCN/$H_2O$, with 0.1% TFA), followed by silica gel column chromatography to provide (2R,3S)-2-(4-(cyclopentylamino)phenyl-3-d)-1-(2-fluoro-6-methylbenzoyl)-N-(4-methyl-3-(trifluoromethyl)phenyl)piperidine-3-carboxamide. MS: (ES) m/z calculated for $C_{33}H_{32}D_3F_4N_3O_2$ [M+H]$^+$ 585.3, found 585.2.

Example 17: Synthesis of (2R,3S)-2-(4-(cyclopentylamino)phenyl-3-d)-1-(2-fluoro-6-(methyl-d$_3$)benzoyl)-N-(4-methyl-3-(trifluoromethyl)phenyl)piperidine-3-carboxamide

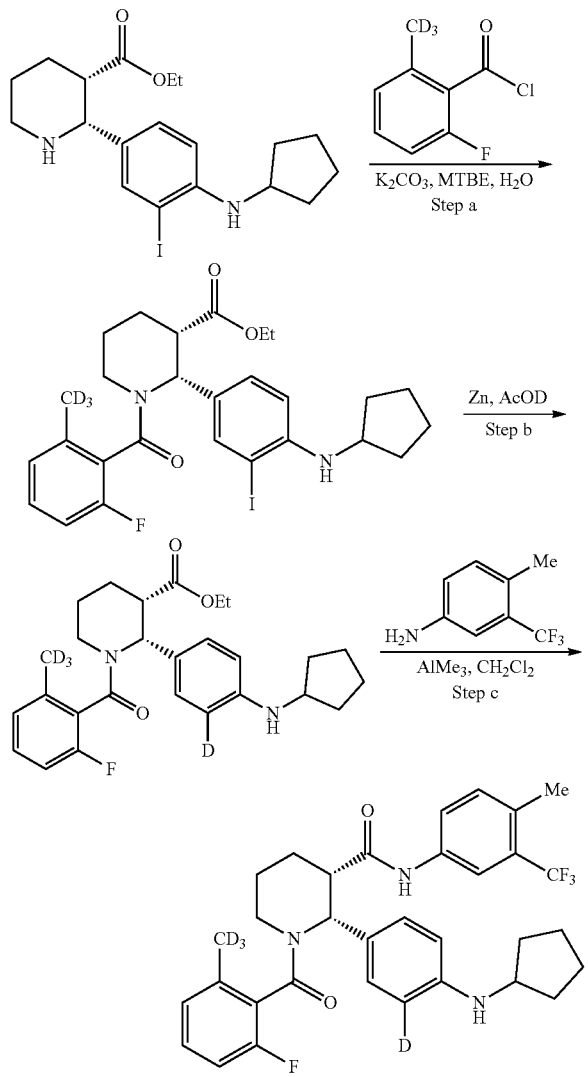

Step a: To a vial containing a solution of ethyl (2R,3S)-2-(4-(cyclopentylamino)-3-iodophenyl)piperidine-3-carboxylate (130 mg, 0.29 mmol) in MTBE (1 mL) was added a solution of potassium carbonate (120 mg, 0.87 mmol) in H$_2$O (1 mL), followed by 2-fluoro-6-(methyl-d$_3$)benzoyl chloride (0.10 g, 0.58 mmol). The contents were stirred at room temperature for 30 min and the mixture was then extracted with EtOAc. The organic phases were combined, dried with Na$_2$SO$_4$, filtered and concentrated. The residue was purified by silica gel column chromatography (30% EtOAc in hexanes) to afford ethyl (2R,3S)-2-(4-(cyclopentylamino)-3-iodophenyl)-1-(2-fluoro-6-(methyl-d$_3$)benzoyl)piperidine-3-carboxylate.

Step b: To a vial containing (2R,3S)-2-(4-(cyclopentylamino)-3-iodophenyl)-1-(2-fluoro-6-(methyl-d$_3$)benzoyl)piperidine-3-carboxylate (107 mg, 0.18 mmol) in acetic acid-d$_4$ (2 mL) was added zinc (185 mg, 2.26 mmol). The mixture was stirred at room temperature for 5 h. The contents were filtered and the filtrate was concentrated. The residue was purified on silica gel column chromatography to yield ethyl (2R,3S)-2-(4-(cyclopentylamino)phenyl-3-d)-1-(2-fluoro-6-(methyl-d$_3$)benzoyl)piperidine-3-carboxylate.

Step c: To a flask containing ethyl (2R,3S)-2-(4-(cyclopentylamino)phenyl-3-d)-1-(2-fluoro-6-(methyl-d$_3$)benzoyl)piperidine-3-carboxylate (76 mg, 0.17 mmol) in CH$_2$Cl$_2$ (1 mL) was added 4-methyl-3-(trifluoromethyl) aniline (37 mg, 0.21 mmol), followed by a solution of 2M AlMe$_3$ in toluene (0.26 mL, 0.52 mmol). The contents were heated at 40° C. for 16 h. An additional portion of 2 M AlMe$_3$ (0.05 mL, 0.1 mmol) was added to the solution and the contents were heated at 40° C. for 16 h. Another portion of 2M AlMe$_3$ (0.05 mL, 0.1 mmol) was added to the solution and the contents were heated at 60° C. for another 24 h. The reaction was quenched by the slow addition of aqueous NaOH. The mixture was filtered and the solids were washed with CH$_2$Cl$_2$. The organic layer was separated and the aqueous layer was extracted with EtOAc. The combined organic layers were dried over Na$_2$SO$_4$, filtered, and concentrated. The residue was purified by HPLC (MeCN/H$_2$O, with 0.1% TFA), followed by silica gel column chromatography to provide (2R,3S)-2-(4-(cyclopentylamino)phenyl-3-d)-1-(2-fluoro-6-(methyl-d$_3$)benzoyl)-N-(4-methyl-3-(trifluoromethyl)phenyl)piperidine-3-carboxamide. MS: (ES) m/z calculated for $C_{33}H_{31}D_4F_4N_3O_2$ [M+H]$^+$ 586.3, found 586.2.

Example 18: Synthesis of (2R,3S)-2-(4-(cyclopentylamino)phenyl-3-d)-1-(2-fluoro-6-methylbenzoyl)-N-(3-hydroxy-4-(hydroxymethyl-d$_2$)phenyl)piperidine-3-carboxamide

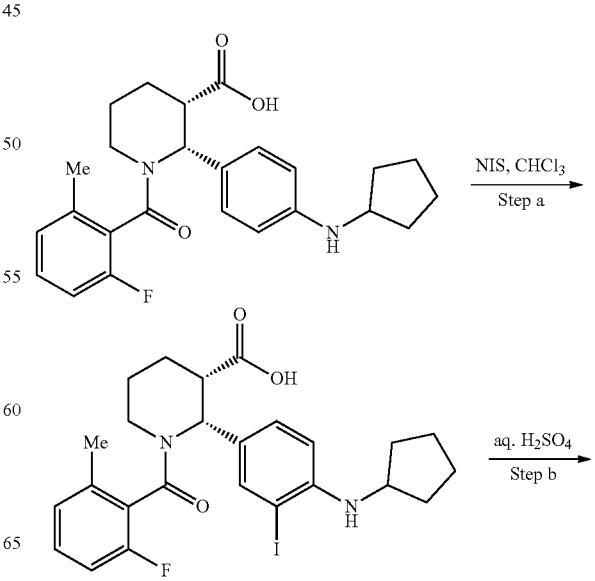

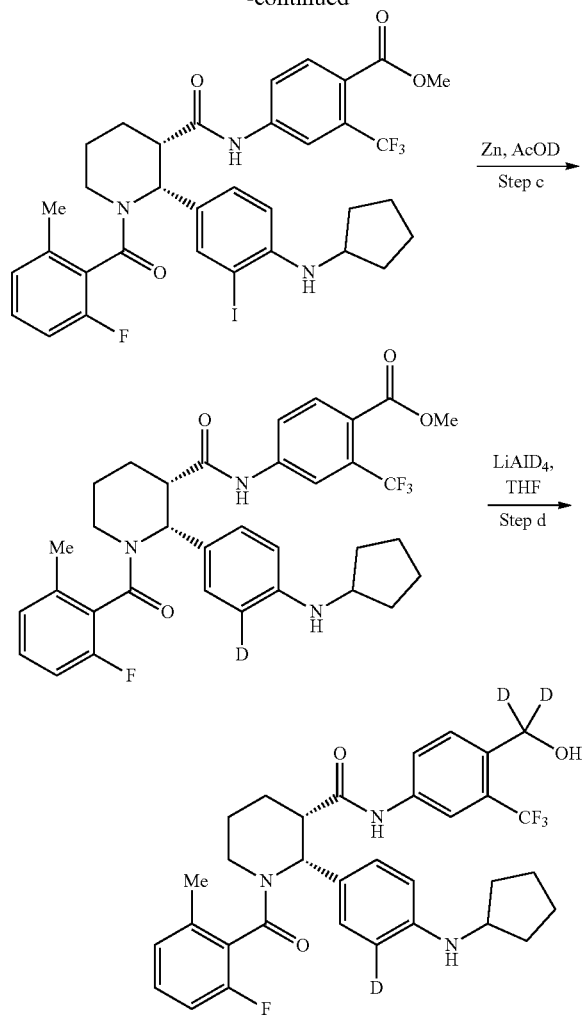

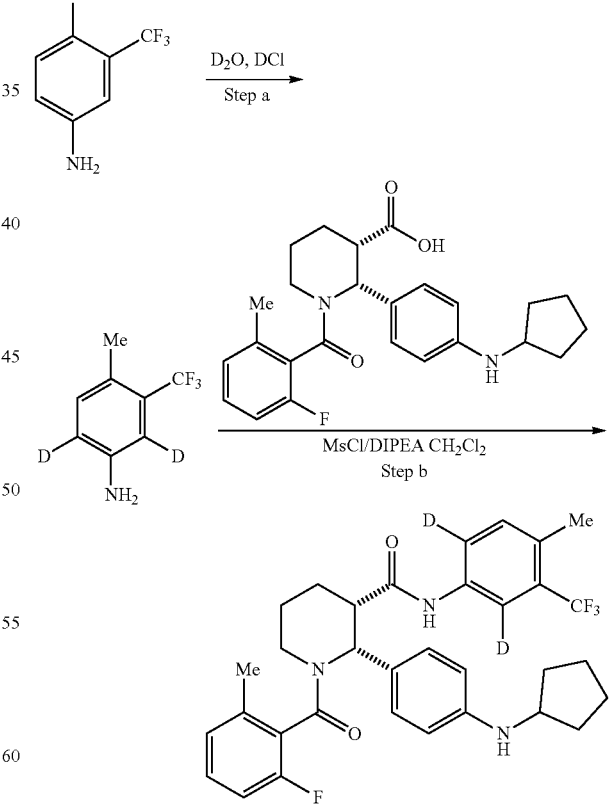

Step a: To a flask containing (2R,3S)-2-(4-(cyclopentylamino)phenyl)-1-(2-fluoro-6-methylbenzoyl)piperidine-3-carboxylic acid (400 mg, 0.94 mmol) in 7 mL of CHCl$_3$ was added N-iodosuccinimide (217 mg, 0.96 mmol). The solution was stirred at room temperature for 2 h then concentrated in vacuo. The residue was purified by silica gel column chromatography (60% EtOAc in hexanes) to give (2R,3S)-2-(4-(cyclopentylamino)-3-iodophenyl)-1-(2-fluoro-6-methylbenzoyl)piperidine-3-carboxylic acid.

Step b: To a flask containing (2R,3S)-2-(4-(cyclopentylamino)-3-iodophenyl)-1-(2-fluoro-6-methylbenzoyl)piperidine-3-carboxylic acid (460 mg, 0.84 mmol) in 2 mL of CH$_2$Cl$_2$ was added methyl 4-amino-2-hydroxybenzoate (220 mg, 1 mmol), followed by N,N-diisopropylethylamine (0.23 mL, 1.3 mmol). The reaction was cooled to 0° C. and methanesulfonyl chloride (0.8 mL, 1 mmol) was added dropwise. After stirring for 1 h at ambient temperature, the contents were concentrated and the crude material was purified by silica gel column chromatography (55% EtOAc in hexanes) to yield methyl 4-((2R,3S)-2-(4-(cyclopentylamino)-3-iodophenyl)-1-(2-fluoro-6-methylbenzoyl)piperidine-3-carboxamido)-2-hydroxybenzoate.

Step c: To a vial containing 4-((2R,3S)-2-(4-(cyclopentylamino)-3-iodophenyl)-1-(2-fluoro-6-methylbenzoyl)piperidine-3-carboxamido)-2-hydroxybenzoate (300 mg, 0.40 mmol) in 0.7 mL of acetic acid-d$_4$ was added zinc (342 mg, 5.2 mmol). The mixture was stirred at room temperature for 3 h. The contents were filtered and the filtrate was concentrated. The residue was purified by silica gel column chromatography to provide methyl 4-((2R,3S)-2-(4-(cyclopentylamino)phenyl-3-d)-1-(2-fluoro-6-methylbenzoyl)piperidine-3-carboxamido)-2-hydroxybenzoate.

Step d: To a vial containing methyl 4-((2R,3S)-2-(4-(cyclopentylamino)phenyl-3-d)-1-(2-fluoro-6-methylbenzoyl)piperidine-3-carboxamido)-2-hydroxybenzoate (200 mg, 0.32 mmol) in 1.6 mL of THF at 0° C. was added LiAlD$_4$ (28 mg, 0.66 mmol). The contents were stirred at 0° C. for 1 h. Upon completion, the reaction was quenched with saturated ammonium chloride. The organic and aqueous layers were separated and the aqueous layer was further extracted with EtOAc. The combined organic layers were dried with Na$_2$SO$_4$, filtered and concentrated. The crude residue was purified by silica gel column chromatography and HPLC (MeCN/H$_2$O, with 0.1% TFA) to yield (2R,3S)-2-(4-(cyclopentylamino)phenyl-3-d)-1-(2-fluoro-6-methylbenzoyl)-N-(3-hydroxy-4-(hydroxymethyl-d2)phenyl)piperidine-3-carboxamide. MS: (ES) m/z calculated for $C_{33}H_{32}D_3F_4N_3O_3$ [M+H]$^+$ 601.3, found 601.2.

Example 19: Synthesis of (2R,3S)-2-(4-(cyclopentylamino)phenyl)-1-(2-fluoro-6-methylbenzoyl)-N-(4-methyl-3-(trifluoromethyl)phenyl-2,6-d$_3$)piperidine-3-carboxamide Step a: To a microwave reaction vial with a magnetic stir bar was charged with 4-methyl-3-(trifluoromethyl)aniline (500 mg, 2.85 mmol), D$_2$O (4 mL) and DCl (0.3 mL, 0.36 mmol). The vial was capped and sealed and heated in a microwave synthesis apparatus for 1 h at 180° C. The reaction mixture was treated with 2 N NaOH (5 mL) and extracted with EtOAc. The organic phase was washed with brine, dried over MgSO$_4$, and filtered. The solvent was removed under reduced pressure to give 4-methyl-3-(trifluoromethyl)benzen-2,6-d$_2$-amine, which was used directly for the next step without further purification. MS: (ES) m/z calculated for C$_8$H$_7$D$_2$F$_3$N [M+H]$^+$ 178.1, found 178.1.

Step b: Methanesufonyl chloride (55 μL, 0.5 mmol) was added to a solution of (2R,3S)-2-(4-(cyclopentylamino)phenyl)-1-(2-fluoro-6-methylbenzoyl)piperidine-3-carboxylic acid (160 mg, 0.38 mmol) and DIPEA (120 μL, 0.68 mmol) in CH$_2$Cl$_2$ (10 mL) at 0° C. The solution was stirred for an addional 10 min, then a slolution of 4-methyl-3-(trifluoromethyl)benzen-2,6-d$_2$-amine (90 mg, 0.5 mmol) in CH$_2$Cl$_2$ (2 mL) and was added, followed by DIPEA (120 μL, 0.68 mmol). The reaction mixture was allowed to warm up to room temperature over 1 h. The reaction mixture was diluted with EtOAc. The organic layer washed with NaHCO$_3$, brine and dried over MgSO$_4$ and filitered. The solvent was removed under reduced pressure and the residue was purified by silica gel flash chromatography (5 to 50% EtOAc in hexanes), followed by HPLC (MeCN/H$_2$O,l with 0.1% TFA) to give (2R,3S)-2-(4-(cyclopentylamino)phenyl)-1-(2-fluoro-6-methylbenzoyl)-N-(4-methyl-3-(trifluoromethyl) phenyl-2,6-d$_2$)piperidine-3-carboxamide. MS: (ES) m/z calculated for C$_{33}$H$_{34}$D$_2$F$_4$N$_3$O$_2$ [M+H]$^+$ 584.3, found 584.2.

Example 20: Synthesis of (2R,3S)-2-(4-(cyclopentylamino)phenyl)-1-(2-fluoro-6-methylbenzoyl)-N-(4-methyl-3-(trifluoromethyl)phenyl-6-d)piperidine-3-carboxamide

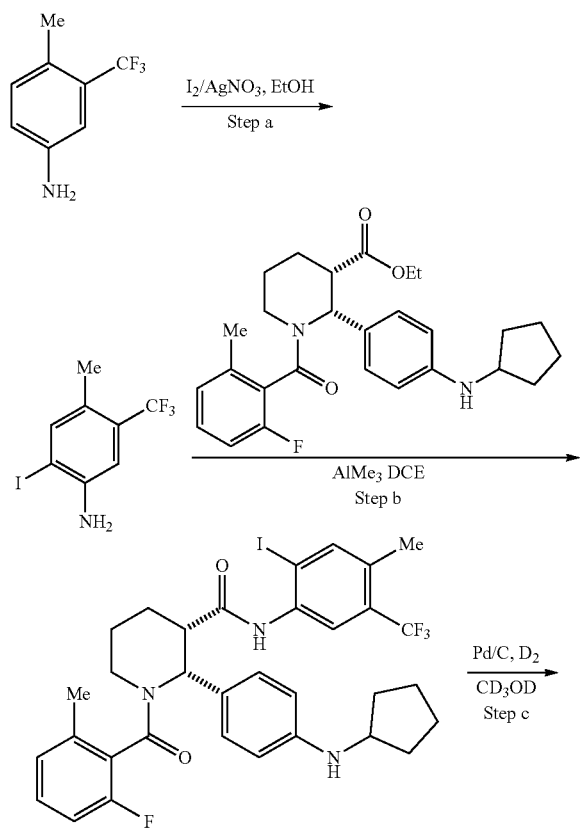

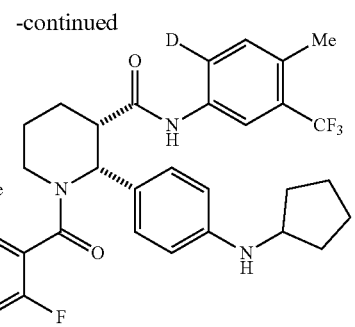

Step a: To a 250 mL flask with a magnetic stir bar was charged with 4-methyl-3-(trifluoromethyl)aniline (1.75 g, 10 mmol), silver nitrate (1.7 g, 10 mmol), iodine (2.54 g, 10 mmol) and EtOH (40 mL). The reaction mixture was stirred at room temperature for 1 h and filtered through Celite. The solvent was removed under reduced pressure and the residue was purified by silica gel flash chromatography (2 to 30% EtOAc in hexanes) to give 2-iodo-4-methyl-5-(trifluoromethyl)aniline. MS: (ES) m/z calculated for C$_8$H$_8$F$_3$IN [M+H]$^+$ 301.9, found 301.9.

Step b: Me$_3$Al (0.4 mL, 0.8 mmol, 2M in toluene) was added to a solution of 2-iodo-4-methyl-5-(trifluoromethyl) aniline (150 mg, 0.5 mmol) in anhydrous dichloroethane (2 mL) at ambient temperature. After stirring for 20 min, a solution of ethyl (2R,3S)-2-(4-(cyclopentylamino)phenyl)-1-(2-fluoro-6-methylbenzoyl)piperidine-3-carboxylate (100 mg, 0.23 mmol) in anhydrous dichloroethane (2 mL) was added. The reaction mixture was stirred at 85° C. for 3 h and cooled to room temperature. The reaction mixture was diluted with CH$_2$Cl$_2$, washed with NaHCO$_3$, brine, dried over MgSO$_4$ and filtered. The solvent was removed under reduced pressure and the residue was purified by silica gel flash chromatography (5 to 50% EtOAc in hexanes) to give (2R,3S)-2-(4-(cyclopentylamino)phenyl)-1-(2-fluoro-6-methylbenzoyl)-N-(2-iodo-4-methyl-5-(trifluoromethyl) phenyl)piperidine-3-carboxamide. MS: (ES) m/z calculated for C$_{33}$H$_{35}$F$_4$IN$_3$O$_2$ [M+H]$^+$ 708.2, found 708.2.

Step c: A suspension of 10% Pd/C (120 mg) in CD$_3$OD (5 mL) was degassed with D$_2$, and then charged with D$_2$ baloon. After stirring at ambient temperature for 1 h, a solution of (2R,3S)-2-(4-(cyclopentylamino)phenyl)-1-(2-fluoro-6-methylbenzoyl)-N-(2-iodo-4-methyl-5-(trifluoromethyl)phenyl)piperidine-3-carboxamide (100 mg, 0.14 mmol) in CD$_3$OD (5 mL) was added. The reaction mixture was stirred at ambient temperature for 2 h and filtered through Celite. The solvent was removed under reduced pressure and the residue was purified by by HPLC (MeCN/ H$_2$O, with 0.1% TFA) to give (2R,3S)-2-(4-(cyclopentylamino)phenyl)-1-(2-fluoro-6-methylbenzoyl)-N-(4-methyl-3-(trifluoromethyl)phenyl-6-d)piperidine-3-carboxamide. MS: (ES) m/z calculated for C$_{33}$H$_{35}$DF$_4$IN$_3$O$_2$ [M+H]$^+$ 583.3, found 583.2.

Example 21: Synthesis of (2R,3S)-2-(4-((cyclopentyl-3,3,4,4-d$_4$)amino)phenyl)-1-(2-fluoro-6-methylbenzoyl)-N-(4-methyl-3-(trifluoromethyl)phenyl)piperidine-3-carboxamide

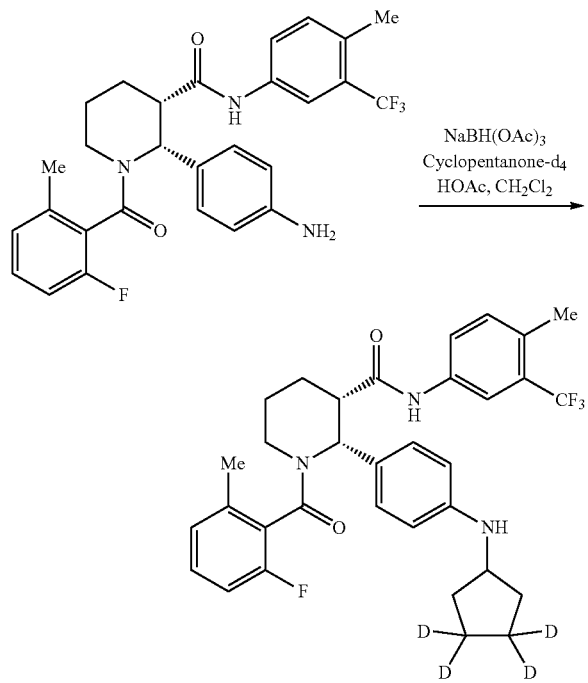

To a 250 mL flask containing aniline (4.36 g, 8.5 mmol), cyclopentanone-3,3,4,4-d$_4$ (2.25 g, 25.5 mmol) and HOAc (0.49 mL, 8.5 mmol) in CH$_2$Cl$_2$ (50 mL) was added NaBH(OAc)$_3$ (5.40 g, 25.5 mmol) portionwise within 15 min. The mixture was stirred for 1 h at −15° C. To the mixture was then added HOAc (0.098 mL, 1.7 mmol), cyclopentanone-3,3,4,4-d$_4$ (0.75 g, 8.5 mmol) and NaBH(OAc)$_3$ (0.54 g, 2.55 mmol). The mixture was allowed to warm to room temperature and stirred for another 4 h. It was quenched with aq. NaHCO$_3$ and extracted with CH$_2$Cl$_2$. The organic layer was dried over Na$_2$SO$_4$, and concentrated in vacuo. The residue was purified according to the following sequence: silica gel flash chromatography (0 to 90% EtOAc in hexanes), recrystallization from 15% H$_2$O in EtOH, silica gel flash chromatography (0 to 50% EtOAc in CH$_2$Cl$_2$) and silica gel flash chromatography (0 to 90% EtOAc in hexanes) to obtain (2R,3S)-2-(4-((cyclopentyl-3,3,4,4-d$_4$)amino)phenyl)-1-(2-fluoro-6-methylbenzoyl)-N-(4-methyl-3-(trifluoromethyl)phenyl)piperidine-3-carboxamide. MS: (ES) m/z calculated for C$_{33}$H$_{31}$D$_4$F$_4$N$_3$O$_2$ [M+H]$^+$ 586.3, found 586.2.

Biological Example 1

This example illustrates the evaluation of the biological activity associated with specific compounds of the invention.

A serial dilution of C5aR compound or an equivalent volume of DMSO was added to freshly-drawn human blood (EDTA as anticoagulant). Separately, recombinant hC5a was diluted with chemotaxis buffer, after which 29 μl of diluted chemokine was placed in the lower wells of a ChemoTX plate (Neuro Probe, Gaithersburg, MD). A 3-μm (pore size) polycarbonate membrane (Neuro Probe, Gaithersburg, MD) was placed onto the plate, and 20 μL of the blood/compound mixture was transferred onto each well of the membrane. The plates were incubated at 37° C. for 90-180 minutes, after which the polycarbonate membranes were removed and 5 μl of the DNA-intercalating agent CyQUANT (Invitrogen, Carlsbad, CA) was added to the lower wells. The amount of fluorescence, corresponding to the number of migrated cells, was measured using a Spectrafluor Plus plate reader (TECAN, San Jose, CA).

Compounds in Table 1 were prepared by methods as described in the Examples, and evaluated according to the assay above. The IC$_{50}$ of the compounds are presented in Table 1 as follows: +++, IC$_{50}$≤100 nM.

TABLE 1

| Compound Number | Structure | Mig IC$_{50}$ (nM) | MS: (ES) m/z [M + H]$^+$ |
|---|---|---|---|
| 1.001 | 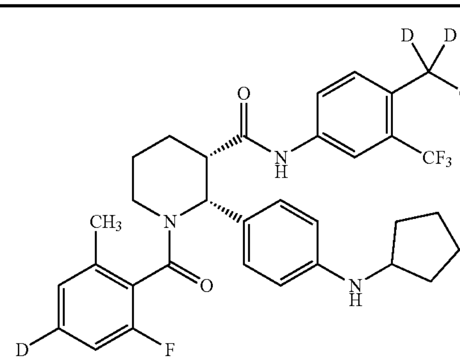 | +++ | 601.2 |

TABLE 1-continued

| Compound Number | Structure | Mig IC$_{50}$ (nM) | MS: (ES) m/z [M + H]$^+$ |
|---|---|---|---|
| 1.002 | 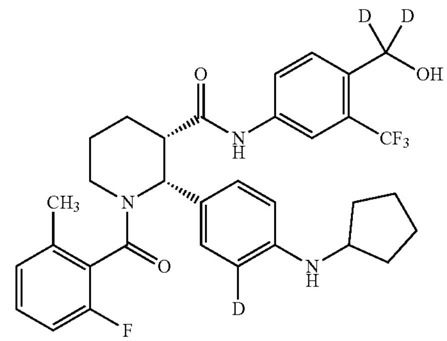 [SMILES: [2H]c1cc([C@H]2[C@@H](C(=O)Nc3ccc(C([2H])([2H])O)c(C(F)(F)F)c3)CCCN2C(=O)c2c(C)cccc2F)ccc1NC1CCCC1] | +++ | 601.2 |
| 1.003 | 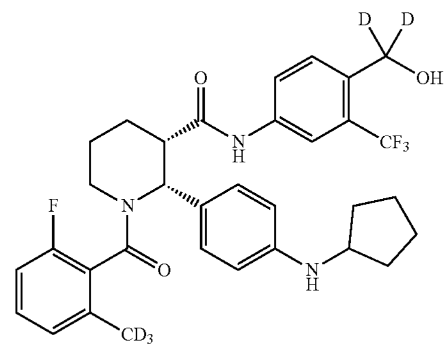 [SMILES: [2H]C([2H])([2H])c1cccc(F)c1C(=O)N1CCC[C@H](C(=O)Nc2ccc(C([2H])([2H])O)c(C(F)(F)F)c2)[C@@H]1c1ccc(NC2CCCC2)cc1] | +++ | 603.3 |
| 1.004 | 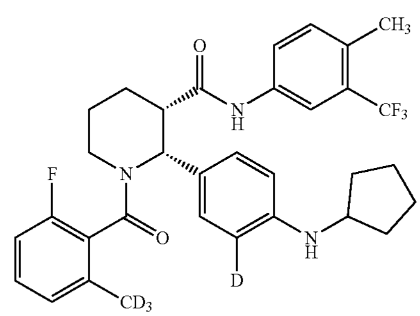 [SMILES: [2H]c1cc([C@H]2[C@@H](C(=O)Nc3ccc(C)c(C(F)(F)F)c3)CCCN2C(=O)c2c(F)cccc2C([2H])([2H])[2H])ccc1NC1CCCC1] | +++ | 586.2 |
| 1.005 | 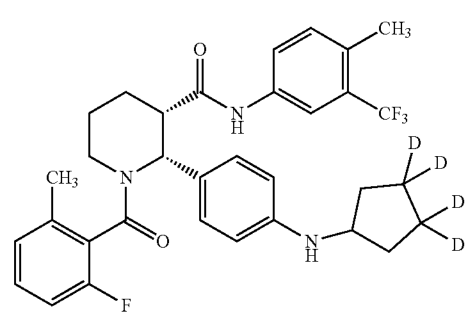 [SMILES: [2H]C1([2H])CC(Nc2ccc([C@H]3[C@@H](C(=O)Nc4ccc(C)c(C(F)(F)F)c4)CCCN3C(=O)c3c(C)cccc3F)cc2)CC1([2H])[2H]] | +++ | 586.2 |

TABLE 1-continued

| Compound Number | Structure | Mig IC$_{50}$ (nM) | MS: (ES) m/z [M + H]$^+$ |
|---|---|---|---|
| 1.006 | 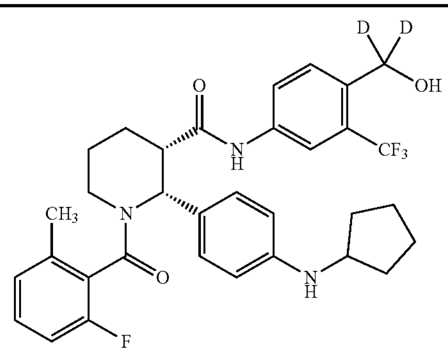 | +++ | 600.2 |
| 1.007 | 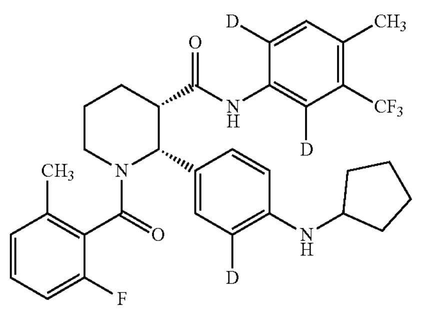 [SMILES: [2H]c1cc([C@H]2[C@@H](C(=O)Nc3c([2H])cc(C)c(C(F)(F)F)c3[2H])CCCN2C(=O)c2c(C)cccc2F)ccc1NC1CCCC1] | +++ | 585.2 |
| 1.008 | 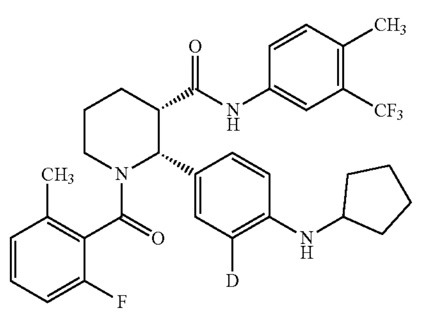 [SMILES: [2H]c1cc([C@H]2[C@@H](C(=O)Nc3ccc(C)c(C(F)(F)F)c3)CCCN2C(=O)c2c(C)cccc2F)ccc1NC1CCCC1] | +++ | 583.2 |
| 1.009 | 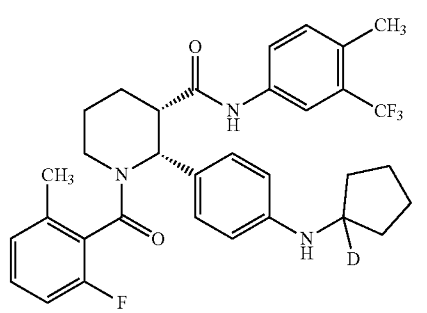 [SMILES: [2H]C1(Nc2ccc([C@H]3[C@@H](C(=O)Nc4ccc(C)c(C(F)(F)F)c4)CCCN3C(=O)c3c(C)cccc3F)cc2)CCCC1] | +++ | 583.2 |
| 1.010 | 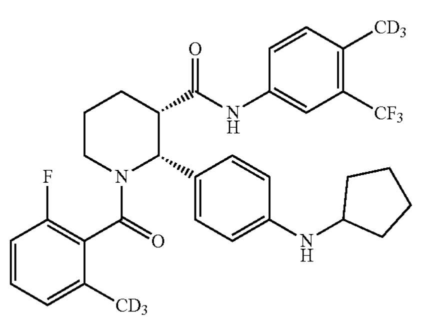 | +++ | 588.3 |

TABLE 1-continued

| Compound Number | Structure | Mig IC$_{50}$ (nM) | MS: (ES) m/z [M + H]$^+$ |
|---|---|---|---|
| 1.011 | 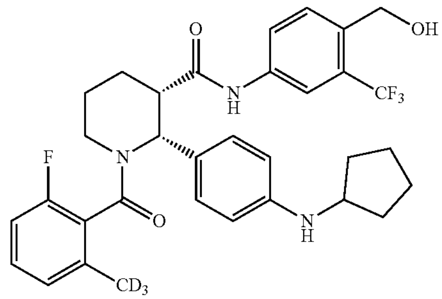 [SMILES: [2H]C([2H])([2H])c1cccc(F)c1C(=O)N1CCC[C@H](C(=O)Nc2ccc(CO)c(C(F)(F)F)c2)[C@@H]1c1ccc(NC2CCCC2)cc1] | +++ | 601.2 |
| 1.012 | 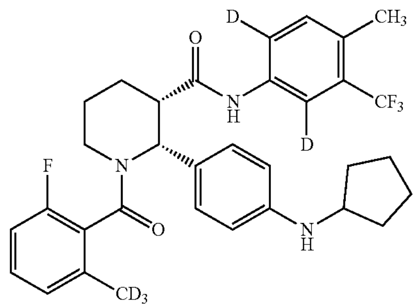 [SMILES: [2H]c1cc(C)c(C(F)(F)F)c([2H])c1NC(=O)[C@H]1CCCN(C(=O)c2c(F)cccc2C([2H])([2H])[2H])[C@H]1c1ccc(NC2CCCC2)cc1] | +++ | 587.3 |
| 1.013 | 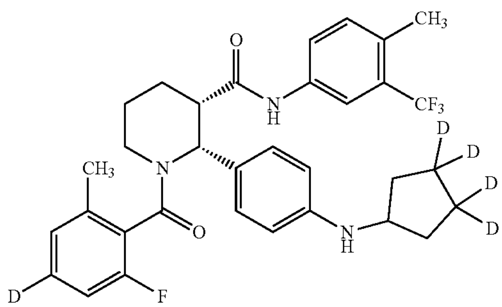 [SMILES: [2H]c1cc(C)c(C(=O)N2CCC[C@H](C(=O)Nc3ccc(C)c(C(F)(F)F)c3)[C@@H]2c2ccc(NC3CC([2H])([2H])C([2H])([2H])C3)cc2)c(F)c1] | +++ | 587.3 |
| 1.014 | 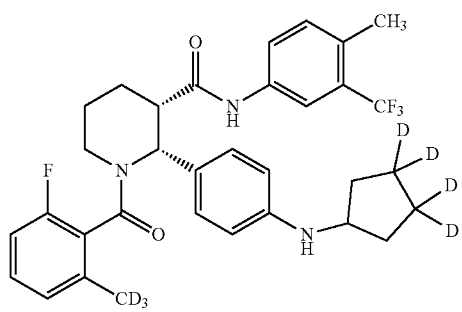 [SMILES: [2H]C([2H])([2H])c1cccc(F)c1C(=O)N1CCC[C@H](C(=O)Nc2ccc(C)c(C(F)(F)F)c2)[C@@H]1c1ccc(NC2CC([2H])([2H])C([2H])([2H])C2)cc1] | +++ | 589.2 |
| 1.015 | 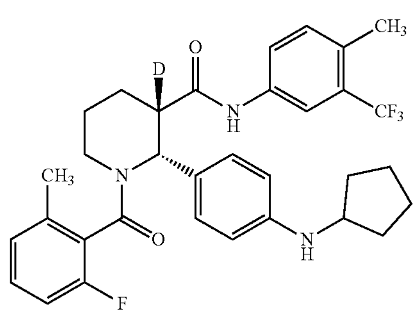 [SMILES: [2H][C@]1(C(=O)Nc2ccc(C)c(C(F)(F)F)c2)CCCN(C(=O)c2c(C)cccc2F)[C@H]1c1ccc(NC2CCCC2)cc1] | +++ | 583.2 |

TABLE 1-continued

| Compound Number | Structure | Mig IC$_{50}$ (nM) | MS: (ES) m/z [M + H]$^+$ |
|---|---|---|---|
| 1.016 | 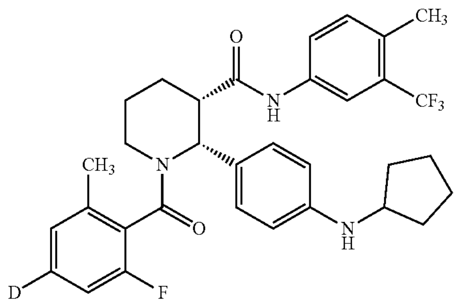 [SMILES: [2H]c1cc(C)c(C(=O)N2CCC[C@H](C(=O)Nc3ccc(C)c(C(F)(F)F)c3)[C@@H]2c2ccc(NC3CCCC3)cc2)c(F)c1] | +++ | 583.2 |
| 1.017 | 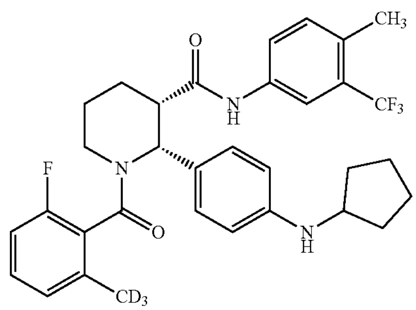 [SMILES: [2H]C([2H])([2H])c1cccc(F)c1C(=O)N1CCC[C@H](C(=O)Nc2ccc(C)c(C(F)(F)F)c2)[C@@H]1c1ccc(NC2CCCC2)cc1] | +++ | 585.2 |
| 1.018 | 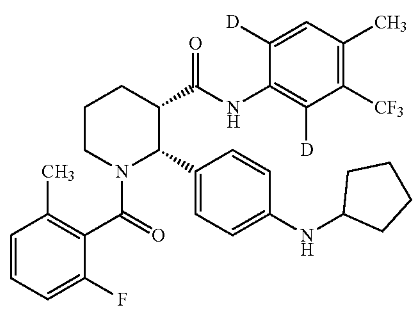 [SMILES: [2H]c1cc(C)c(C(F)(F)F)c([2H])c1NC(=O)[C@H]1CCCN(C(=O)c2c(C)cccc2F)[C@H]1c1ccc(NC2CCCC2)cc1] | +++ | 584.2 |
| 1.019 | 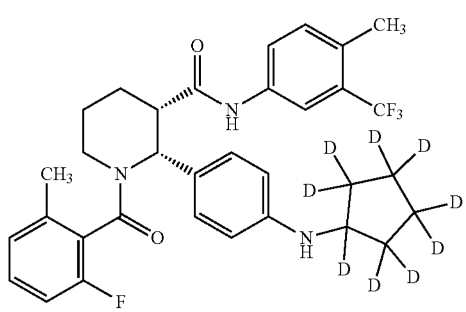 [SMILES: [2H]C1([2H])C([2H])([2H])C([2H])([2H])C([2H])(Nc2ccc([C@H]3[C@@H](C(=O)Nc4ccc(C)c(C(F)(F)F)c4)CCCN3C(=O)c3c(C)cccc3F)cc2)C1([2H])[2H]] | +++ | 591.3 |
| 1.020 | 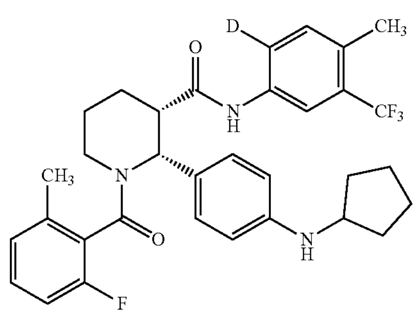 [SMILES: [2H]c1cc(C)c(C(F)(F)F)cc1NC(=O)[C@H]1CCCN(C(=O)c2c(C)cccc2F)[C@H]1c1ccc(NC2CCCC2)cc1] | +++ | 583.2 |

TABLE 1-continued
| Compound Number | Structure | Mig IC$_{50}$ (nM) | MS: (ES) m/z [M + H]$^+$ |
|---|---|---|---|
| 1.021 | 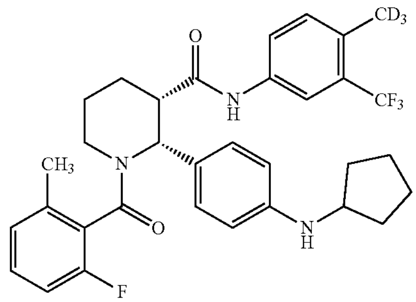 [SMILES: [2H]C([2H])([2H])c1ccc(NC(=O)[C@H]2CCCN(C(=O)c3c(C)cccc3F)[C@H]2c2ccc(NC3CCCC3)cc2)cc1C(F)(F)F] | +++ | 585.3 |
What is claimed is:
1. A compound or a pharmaceutically acceptable salt thereof, selected from the group consisting of
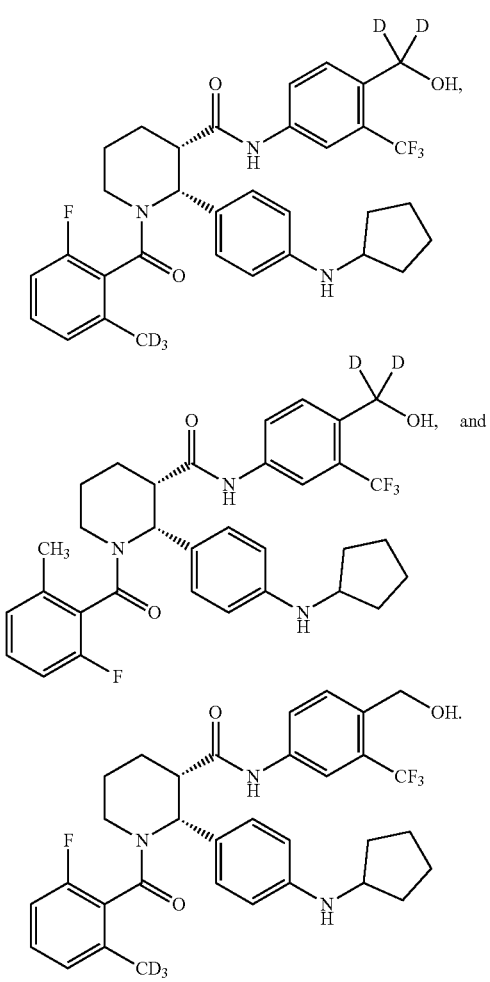
2. A compound or a pharmaceutically acceptable salt thereof, selected from the group consisting of
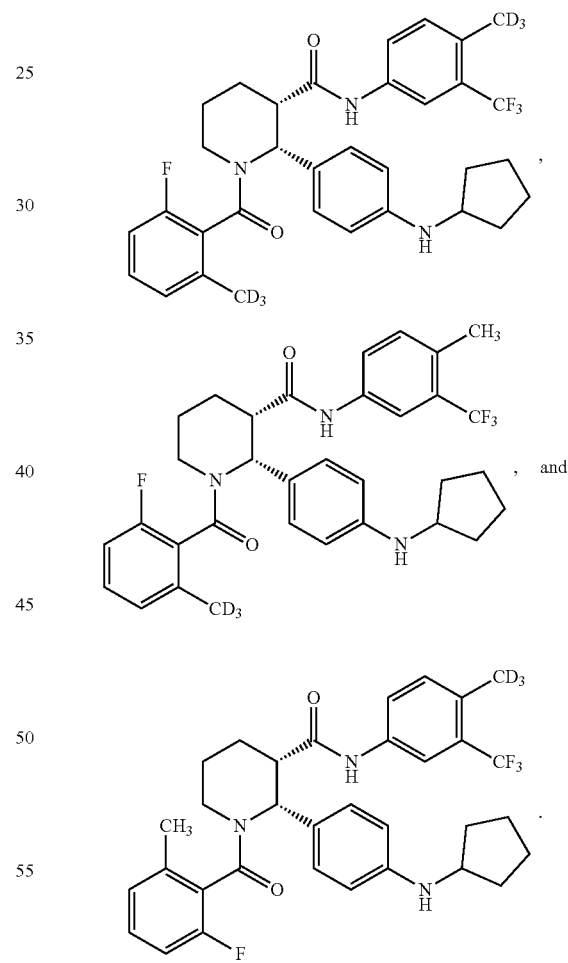
* * * * *